United States Patent
Sasaki

(10) Patent No.: US 12,193,804 B2
(45) Date of Patent: Jan. 14, 2025

(54) SUBJECT MOTION MEASURING APPARATUS, SUBJECT MOTION MEASURING METHOD, NON-TRANSITORY COMPUTER READABLE MEDIUM AND IMAGING SYSTEM

(71) Applicants: CANON KABUSHIKI KAISHA, Tokyo (JP); CANON MEDICAL SYSTEMS CORPORATION, Tochigi (JP)

(72) Inventor: Toru Sasaki, Kanagawa (JP)

(73) Assignees: CANON KABUSHIKI KAISHA, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 401 days.

(21) Appl. No.: 17/547,329

(22) Filed: Dec. 10, 2021

(65) Prior Publication Data

US 2022/0183583 A1     Jun. 16, 2022

(30) Foreign Application Priority Data

Dec. 15, 2020   (JP) .................................. 2020-207809

(51) Int. Cl.
*A61B 5/055*     (2006.01)
*A61B 5/00*      (2006.01)
(Continued)

(52) U.S. Cl.
CPC ............ *A61B 5/055* (2013.01); *A61B 5/0077* (2013.01); *G01R 33/5608* (2013.01); *G06T 7/0012* (2013.01)

(58) Field of Classification Search
CPC .................. A61B 5/055; A61B 5/0077; G01R 33/5608; G06T 7/0012
(Continued)

(56) References Cited

U.S. PATENT DOCUMENTS

| 8,121,361 B2 | 2/2012 | Ernst et al. |
| 2008/0071507 A1* | 3/2008 | Hodgins .................. G01S 5/16 |
| | | 703/6 |

(Continued)

FOREIGN PATENT DOCUMENTS

EP     3581109 A1     12/2019

OTHER PUBLICATIONS

Oline Vinter Olesen et al., "Motion Tracking for Medical Imaging: A Nonvisible Structured Light Tracking Approach" IEEE Transactions on Medical Imaging, Jan. 2012, vol. 31, No. 1, pp. 79-87.

(Continued)

*Primary Examiner* — Gabriel I Garcia
(74) *Attorney, Agent, or Firm* — Carter, DeLuca & Farrell LLP

(57) ABSTRACT

A subject motion measuring apparatus includes a camera for imaging a subject, at least one memory storing a program, and at least one processor which, by executing the program, causes the subject motion measuring apparatus to acquire three-dimensional coordinate data on a patch set in frame data included in moving image data imaged by the camera. The processor tracks the patch in the moving image data imaged by the camera and generates motion data on the subject on the basis of the three-dimensional coordinate data on the tracked patch.

25 Claims, 22 Drawing Sheets

(51) Int. Cl.
    *G01R 33/56*    (2006.01)
    *G06T 7/00*     (2017.01)

(58) Field of Classification Search
    USPC .......................................................... 382/128
    See application file for complete search history.

(56) References Cited

U.S. PATENT DOCUMENTS

| | | | |
|---|---|---|---|
| 2017/0091529 A1* | 3/2017 | Beeler | G06T 7/246 |
| 2017/0278237 A1* | 9/2017 | Lovberg | G06T 7/73 |
| 2020/0022654 A1* | 1/2020 | Yu | A61B 5/1121 |
| 2021/0397859 A1* | 12/2021 | Arora | G06V 40/19 |
| 2021/0401298 A1* | 12/2021 | Levi | A61B 5/7225 |

OTHER PUBLICATIONS

Notice of Reasons for Refusal issued by the Japanese Patent Office on Aug. 13, 2024 in corresponding JP Patent Application No. 2020-207809, with English translation.

* cited by examiner

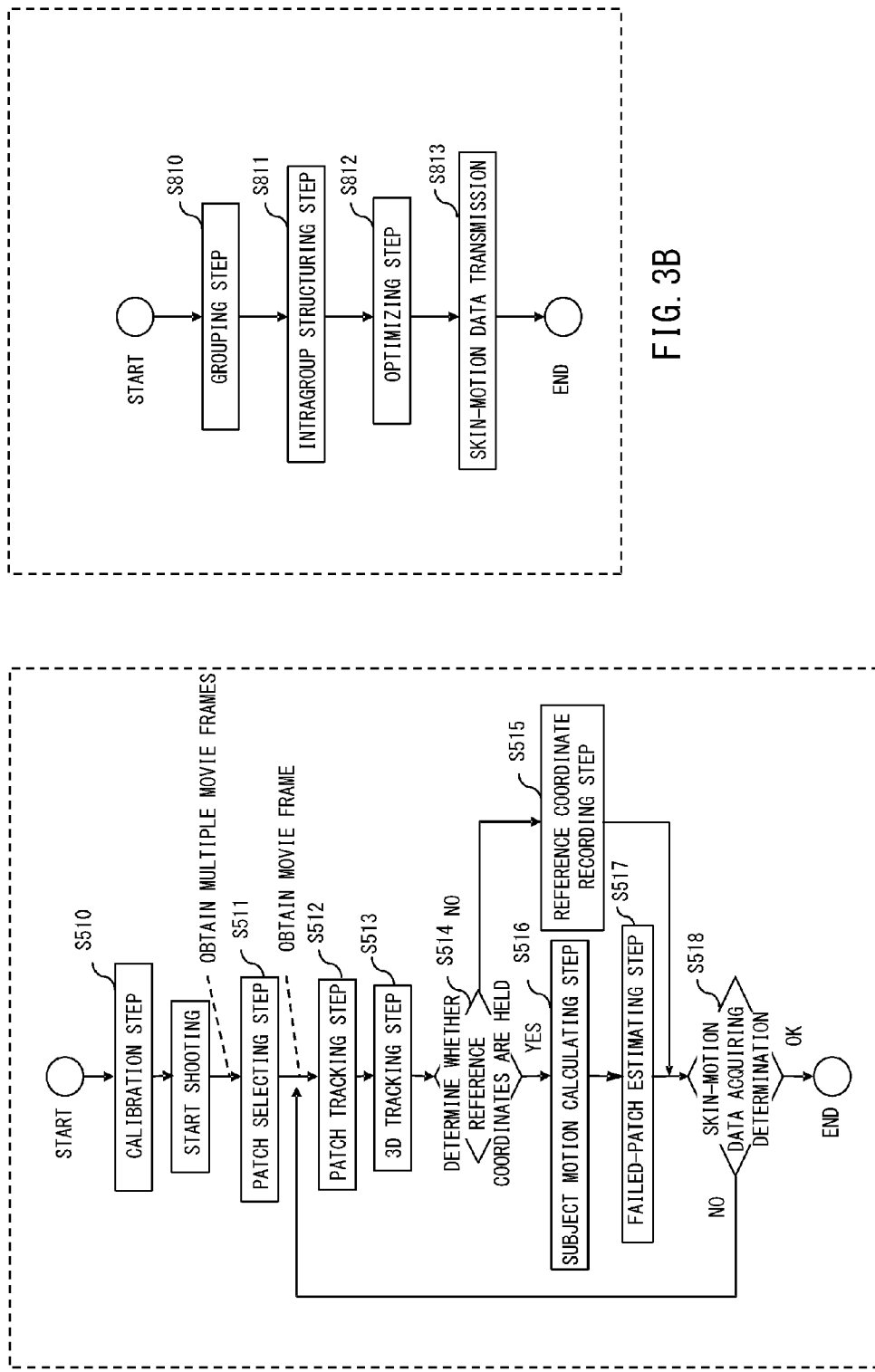

|  | $t_1$ | $t_1+a$ | $t_1+b$ | $t_1+c$ | $t_2$ | $t_2+a$ | $t_2+b$ | $t_2+c$ |
|---|---|---|---|---|---|---|---|---|
| PATCH1 | A:(-, -) | B:(120, 100) |  |  | A:(100, 110) | B:(120, 110) |  |  |
| PATCH2 | A:(500, 100) | B:(522, 100) |  |  | A:(-, -) | B:(522, 100) |  |  |
| PATCH3 | A:(100, 900) | B:(150, 900) |  |  | A:(100, 910) | B:(150, 910) |  |  |
| PATCH4 | A:(500, 900) | B:(-, -) |  |  | A:(500, 900) | B:(552, 900) |  |  |
| PATCH5 |  |  | C:(80, 110) | D:(90, 110)<br>E:(-, -) |  |  | C:(-, -) | D:(90, 110)<br>E:(100, 110) |
| PATCH6 |  |  | C:(-, -) | D:(522, 100)<br>E:(522, 100) |  |  | C:(500, 100) | D:(532, 100)<br>E:(532, 100) |
| PATCH7 |  |  | C:(82, 910) | D:(90, 910)<br>E:(-, -) |  |  | C:(100, 910) | D:(100, 910)<br>E:(-, -) |
| PATCH8 |  |  | C:(450, 900) | D:(-, -)<br>E:(500, 910) |  |  | C:(500, 900) | D:(552, 900)<br>E:(-, -) |

FIG. 8

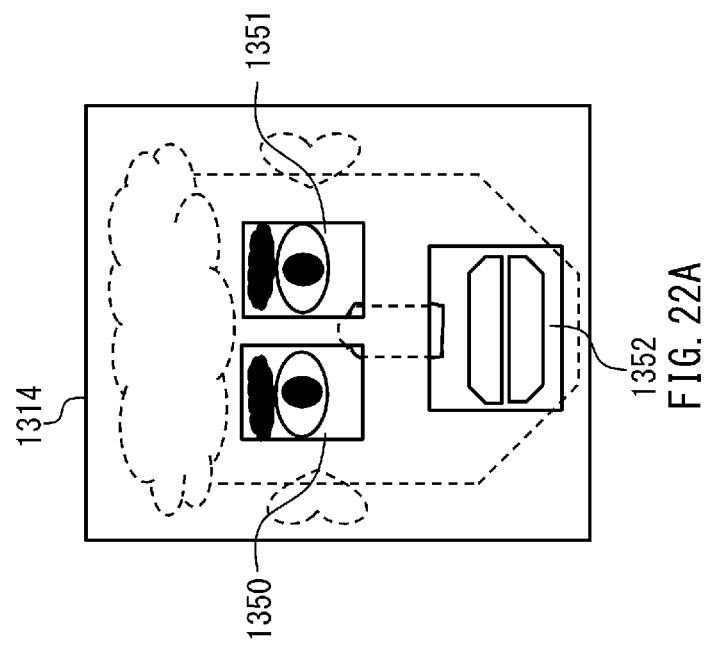
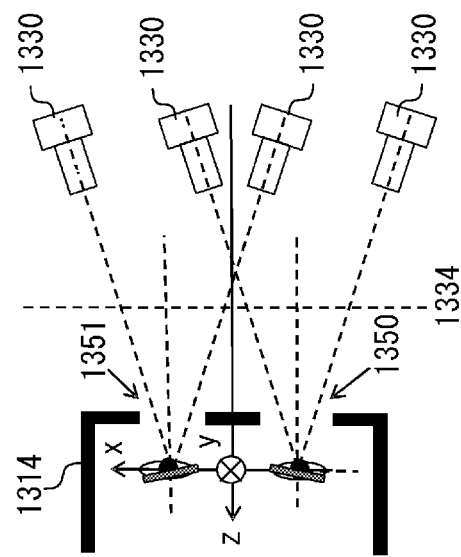
FIG. 22A
FIG. 22B

SUBJECT MOTION MEASURING APPARATUS, SUBJECT MOTION MEASURING METHOD, NON-TRANSITORY COMPUTER READABLE MEDIUM AND IMAGING SYSTEM

BACKGROUND OF THE INVENTION

Field of the Invention

The present invention relates to a technique for measuring a motion of a subject.

Description of the Related Art

In recent years, magnetic resonance imaging apparatuses with static magnetic field strength of 3 T (Tesla) are commercially available and the resolutions of output images have been increased. However, such magnetic resonance imaging apparatuses may clearly generate artifacts that are relatively indistinct in the conventional art. This is a new challenge to be solved.

As a cause of such artifacts, head motions in a head coil are known. Approaches to correcting the gradient magnetic fields of magnetic resonance imaging apparatuses have been made according to head motions measured by cameras.

The specification of U.S. Pat. No. 8,121,361 discloses a method of detecting head motions according to a difference in marker position between movie frames by capturing the images of faces, on which markers called retro-grate reflectors (RGRs) are attached, with a camera from the outside of a head coil. RGRs are markers that detect positions by using moiré fringes, thereby accurately measuring positions.

Although markers are important for improving detection accuracy, markerless methods have been also examined in order to save time and effort in attachment and detachment to and from the face of a subject and avoid a stimulus to a skin at a site of attachment.

O. V. Olesen et al., "Motion tracking for medical imaging: a nonvisible structured light tracking approach", IEEE Trans. on Med. Imag., vol. 31, 79-87 (2012) discloses a method of measuring a three-dimensional shape on a surface around a nose with patterned illumination and detecting head motions, based on a difference between the three-dimensional shapes of different movie frames.

SUMMARY OF THE INVENTION

According to an aspect of the present disclosure, it is provided a subject motion measuring apparatus including a camera for imaging a subject, at least one memory storing a program, and at least one processor which, by executing the program, causes the subject motion measuring apparatus to acquire three-dimensional coordinate data on a patch set in frame data included in moving image data imaged by the camera, wherein the processor tracks the patch in the moving image data imaged by the camera and generates motion data on the subject on the basis of the three-dimensional coordinate data on the tracked patch.

Further features of the present invention will become apparent from the following description of exemplary embodiments with reference to the attached drawings.

BRIEF DESCRIPTION OF THE DRAWINGS

FIGS. 3A and 3B are flowcharts indicating examples of a pre-tracking step and a skin-motion data creating step;

FIG. 8 illustrates an example of the results of the patch tracking step;

FIGS. 22A and 22B are explanatory drawings illustrating the relationship between the cameras and the openings of a head coil.

DESCRIPTION OF THE EMBODIMENTS

An object of the present invention is to provide a technique that can measure the motions of a subject with high accuracy according to a markerless method.

[Subject Motion Measuring Method]

The outline of a subject motion measuring method, a subject motion measuring apparatus, and an imaging system according to an embodiment of the present invention will be described below. The present invention is not limited thereto. The subject motion measuring method according to the embodiment of the present invention will be described below with reference to the accompanying drawings.

<Terms Used for Explaining the Subject Motion Measuring Method>

The present specification describes first imaging means for optically imaging a subject to measure a motion of the subject and second imaging means for imaging the inside of the subject. The former is, for example, a camera, and the latter is, for example, a modality such as a magnetic resonance imaging apparatus. To discriminate between the means, the former is described using terms such as "camera", "imaging means", and "shooting", and the latter is described using terms such as "modality", "imaging apparatus", "imaging means", and "imaging" in the present specification.

"Subject" is an object of motion measurement, that is, an object to be imaged by a camera serving as the first imaging means. Typically, a part of a subject (living body) corresponds to a subject. In the following embodiment, "a part around an eye" on the head of a human body is illustrated as an example of a subject. The subject is not limited thereto. The subject may be a head, a face, a part of a face (a part around a face organ), a chest, an abdomen, an upper limb, a lower limb, or other body parts. In the present measurement method, a motion of an overall subject (referred to as "overall motion") and a local motion on the surface of the subject (referred to as "local motion") are described as equivalent motions. A local motion can be regarded as a change of a point on a subject or the position/posture of a small region in a coordinate system. For example, if "a part around an eye" is a subject, a change of the position/posture of a part around an eye according to a head motion (a translation/rotation of a head) corresponds to an overall motion, whereas a motion of a skin around organs such as an eye and an eyebrow corresponds to a local motion.

Figure 1C:
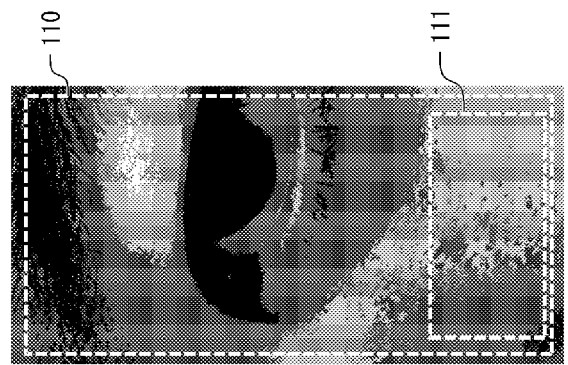
FIGS. 1A to 1C are explanatory drawings illustrating the positional relationship between cameras and a head and the shooting ranges of the cameras.
Figure 1B:
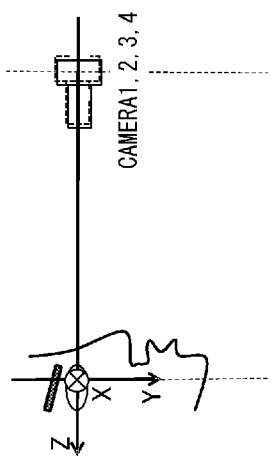
Figure 1A:
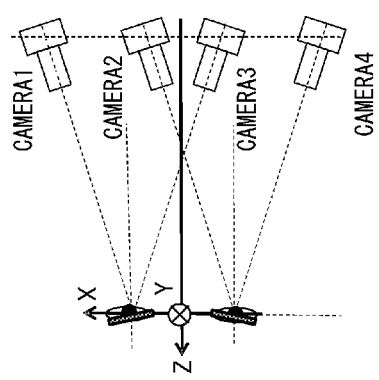

Moving image data used in the subject motion measuring method will be described below. The moving image data is obtained by imaging a part around an eye, which is a subject, in different directions with a plurality of cameras. One eye is imaged by two or more cameras or both eyes are each imaged by two or more cameras. For example, if both eyes are each imaged with two cameras, the cameras are disposed as illustrated in FIG. 1A when viewed from above a head. The cameras are disposed as illustrated in FIG. 1B when viewed in the lateral direction of the head. Computational complexity for determining a parallax can be reduced by a method of projecting a pattern to a subject with a projector (a so-called active stereo method) in addition to a method using two or more cameras (a so-called passive stereo method). FIG. 1A illustrates a layout example including only the cameras. First image data and second image data that are captured by a plurality of cameras are image data imaged from different positions. The first image data and the second image data are image data obtained by imaging a part around a predetermined part of a subject in different directions. In the first image data and the second image data, the same region of the subject is imaged.

The frame rate of the moving image data can be optionally selected but is desirably set at 50 fps or more in order to smoothly measure a motion of a head (skin). Image data (hereinafter referred to as a movie frame) included in the moving image data desirably has a large number of pixels but the number of pixels is limited by the frame rate. The number of pixels is, for example, about one megapixel (about 1300×800 pixels).

The imaging magnification of the camera is selected such that a part around a movie frame (a part remote from the center of an image) includes textures (the pattern of an eyebrow or a skin). The texture is used as a marker of tracking. Some textures on parts (an eye and a lower eyelid) that move quickly with large deformations are not suitable for tracking. Thus, as illustrated in FIG. 1C, a region 110 including an eye at the center or a region 111 not including an eye may serve as the range of a movie frame.

The movie frames of a subject imaged by two cameras at different angles include the displaced subject. The displacement is called a parallax that appears according to a difference in the height of the surface of the subject (depth map).

Figure 2:
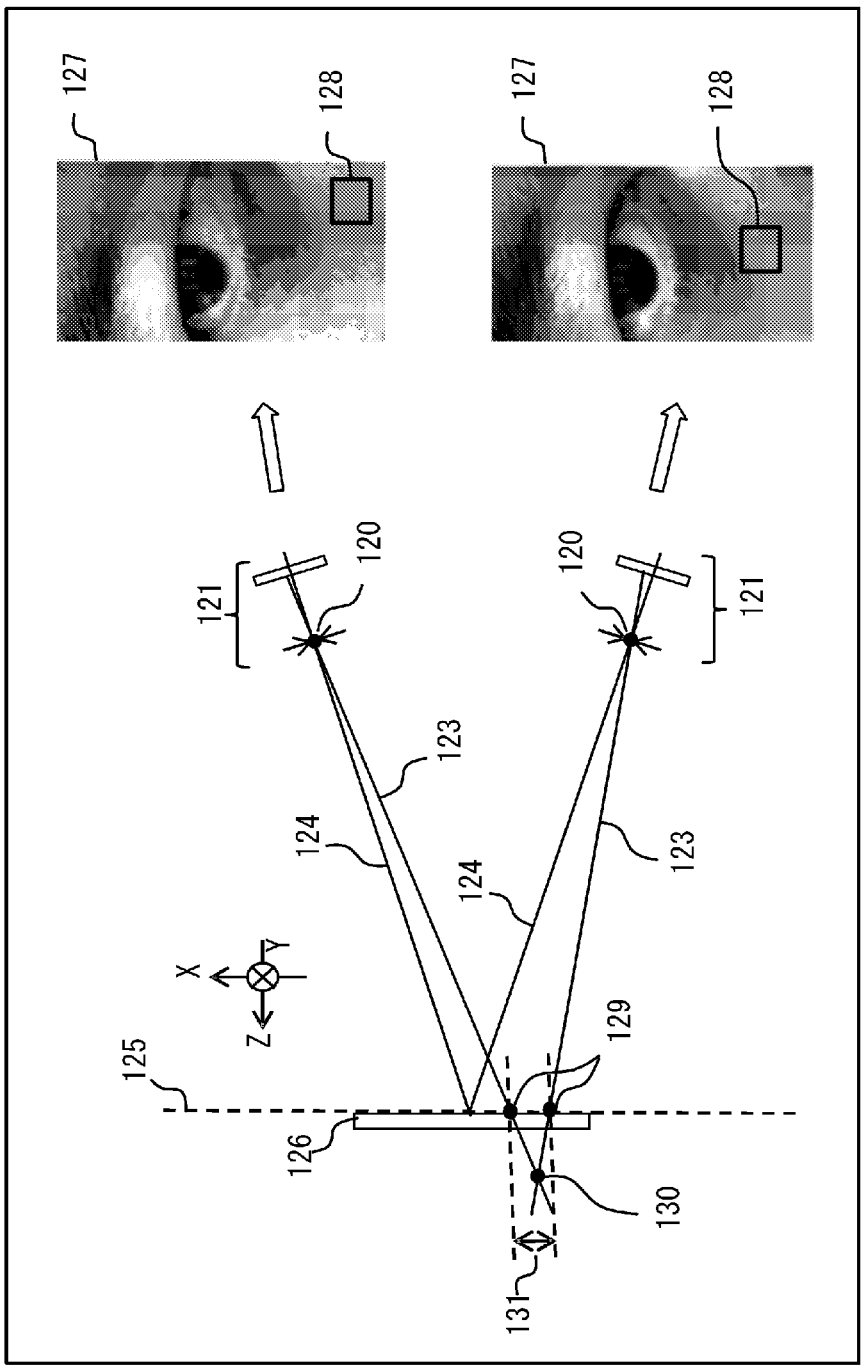
FIG. 2 is an explanatory drawing of a subject motion measuring method.

In the tracking, three-dimensional coordinate data on pixel sections (hereinafter referred to as patches or small regions) including the textures is generated by using the parallax (FIG. 2). In the calculation of a parallax 131, an image 126 (hereinafter referred to as reference-plane image data 127) is created by projecting a movie frame to a plane (hereinafter referred to as a reference plane 125) shared by cameras 121, and a difference in the position of a patch 128, which is included in pieces of the reference-plane image data 127, is determined. The reference plane 125 is a plane that approximates the subject or a plane parallel to the plane. The three-dimensional coordinates of a patch 130 on the subject are located at an intersection point of a principal ray 123 passing through a diaphragm center 120 of one of the cameras and the position of a patch 129 on the reference plane 125 and a principal ray 123 passing through a diaphragm center 120 of the other camera and the position of a patch 129 on the reference plane 125. The direction of the parallax 131 can be adjusted by the direction of an optical axis 124 of each camera and the coordinates of the diaphragm center 120. The direction of the parallax 131 may be adjusted in parallel with the axis of coordinates (horizontal axis) of the movie frame so as to facilitate the generation of three-dimensional coordinate data on the patch.

The coordinate axes of the three-dimensional coordinate data include the X and Y axes in the reference plane 125 and the Z axis parallel to the normal of the reference plane 125. During the selection and tracking of patches, two-dimensional coordinate data in the reference-plane image data is used. The coordinate axes of the two-dimensional coordinate data are identical to the X and Y axes of the three-dimensional coordinate data. The two-dimensional coordinate data is mainly generated in pixels. Thus, the units of generation are frequently different from those in the generation of the three-dimensional coordinate data. In a description of the generation of the three-dimensional coordinate data based on the two-dimensional coordinate data, the units for the three-dimensional coordinate data are used without any additional explanation.

<Flow of Overall Subject Motion Measuring Method>

The flow of the subject motion measuring method according to the present embodiment will be described below. Three-dimensional coordinate data on a patch (small region) is acquired, the patch being set in frame data included in moving image data captured by the camera. The patch is then tracked in the moving image data imaged by the cameras. Thereafter, motion data on a subject is generated based on the three-dimensional coordinate data on the tracked patch. Specifically, three-dimensional coordinate data on patches set in the first image data and the second image data is acquired based on a parallax between the first image data and the second image data in moving image data imaged by the cameras. From the three-dimensional coordinate data on the patches and reference coordinate data serving as a criterion for the subject, a translation and a rotation of the subject are generated. The patches included in the first image data and the second image are identical in size and shape.

The patch is a small region set in a band region in the frame data. The patch is set in a band region around a predetermined part of the subject. In the present embodiment, a plurality of patches are set. The patches are spaced apart a predetermined distance or longer from one another and are set in regions that are not affected by the motion of a skin. The predetermined part is a part that can be imaged by the cameras from an opening of a receiving coil. For example, the predetermined part is an eye or the nose of the subject.

Referring to FIG. 3A, an example of the process of a tracking step will be specifically described below. In a calibration step S510, photography-system parameters (the direction vector of an optical axis for each of the cameras and the diaphragm center coordinates) are obtained before a moving image is captured. The photography-system parameters are generated based on a design value or a measured value of a camera optical system or are generated based on the position of a marker on a movie frame, the marker being included in a imaged calibration chart. It is not always necessary to perform the calibration step S510 each time a head motion is measured. If the photography-system parameters apparently have no changes, step S510 can be omitted.

In a patch selecting step S511 after the start of the shooting of a moving image, for the cameras that photograph the same subject, a plurality of patches to be tracked are selected based on movie frames at close shooting times. In a patch tracking step S512, two-dimensional coordinate data on the patches that are selected in the patch selecting step S511 and are moved by a subject or skin motion is measured from the movie frames based on textures included in the patches. The two-dimensional coordinate data is recorded in an array. In a 3D tracking step S513, three-dimensional coordinate data on the patches is generated based on the two-dimensional coordinate data on the patches captured by each of the cameras and is recorded in an array each time the movie frame is imaged.

In reference-coordinate holding determination S514, it is determined whether the three-dimensional coordinate data on the patches (hereinafter referred to as reference coordinate data) is held as a reference head motion (a translation of 0 mm, a rotation of 0 deg.). If the three-dimensional coordinate data is not held, the reference coordinate data is recorded in the array in a reference-coordinate recording step S515. The reference coordinate data may be three-dimensional coordinate data on patches obtained at present. If the reference coordinate data is held, a subject motion generating step S516 is performed. In the subject motion generating step S516, subject motion data is generated from the three-dimensional coordinate data on the patches obtained at present and three-dimensional coordinate values included in the reference coordinate data.

In a failed-patch estimating step S517, the two-dimensional coordinates of patches having moved out of the movie frame and patches failed to be calculated in the patch tracking step S512 are estimated, and the coordinates are added to the two-dimensional coordinate data recorded in the patch tracking step S512. The estimated two-dimensional coordinate data is used when the patch tracking step S512 is performed on a movie frame at a subsequent shooting time. In the failed-patch estimating step S517, if a patch (first patch) set in frame data on a moving image moves out of the frame, the position of the patch (first patch) is estimated based on the reference coordinate data serving as a criterion for the subject. In the failed-patch estimating step S517, the position of the patch (first patch) having moved out of the frame may be estimated based on a patch (second patch) in the frame, from among multiple patches. Specifically, the position of the patch having moved out of the frame is estimated in the frame based on the center coordinates of the patches. When the patch (first patch) enters the frame, the tracking of the patch (first patch) is immediately restarted.

In a skin-motion data acquiring determination S518, it is determined whether creation completion notification has been transmitted. In the absence of the creation completion notification, the process returns to the patch tracking step S512 for a movie frame at a subsequent shooting time.

<Patch Selecting Step of the Tracking Step>

Figure 4A:
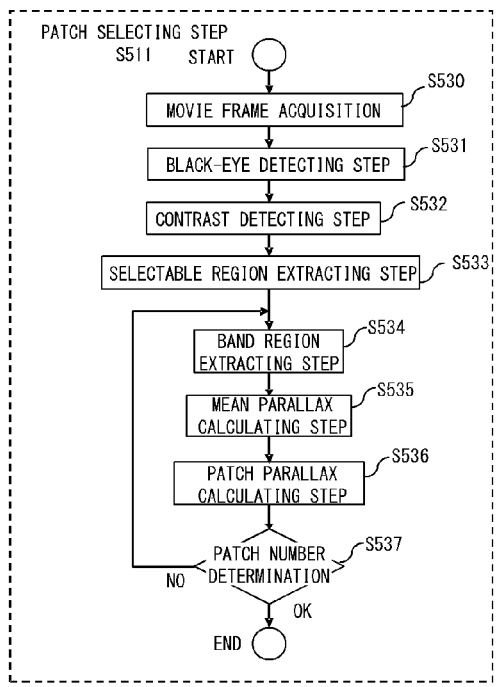
FIGS. 4A to 4E are flowcharts indicating an example of the pre-tracking step.

Referring to FIG. 4A, an example of the process of the patch selecting step S511 will be described below. In movie frame acquisition S530, movie frames at an initial shooting time are obtained for each of the cameras.

In a black-eye detecting step S531, the position and size of a black eye are detected in the movie frames, and some of the movie frames are selected with the black eye located near the centers of the movie frames. The black eye can be detected by, for example, thresholding on pixel values. If the movie frames do not include eyes or the position of an eye on a fixed head is unchanged in the movie frames, the black-eye detecting step S531 can be omitted.

In a contrast detecting step S532, the contrast of skin textures included in the movie frames obtained in the black-eye detecting step S531 (if omitted, the movie frame acquisition S530) is calculated. Subsequently, a movie frame having a high contrast is selected (a movie frame at the same shooting time is selected for each of the cameras). Hence, movie frames with small motion blurs can be selected. The contrast can be calculated by, for example, Normalized variance provided by the following Formula 1.

$$\text{Normalized variance} = \frac{1}{H \cdot W \cdot \mu} \sum_x \sum_y (I(x, y) - \mu)^2 \quad \text{(Formula 1)}$$

where I(x,y) is the pixel value distribution of an image including a skin texture, H and W are the number of pixels in the vertical direction of the image and the number of pixels in the horizontal direction of the image, and $\mu$ is the mean value of pixel values included in the image.

In a selectable region extracting step S533, the reference-plane image data (hereinafter referred to as a selectable region) is created based on pixels around the movie frame selected in the contrast detecting step S532. As illustrated in FIG. 5A, upper and lower selectable regions desirably have the same size. When the reference-plane image data is created, noise may be simultaneously removed from the movie frame. For example, noise in a fixed pattern may cause an error during parallax calculation or patch tracking, which will be described later, and thus the noise is removed using a median filter.

Figure 5B:
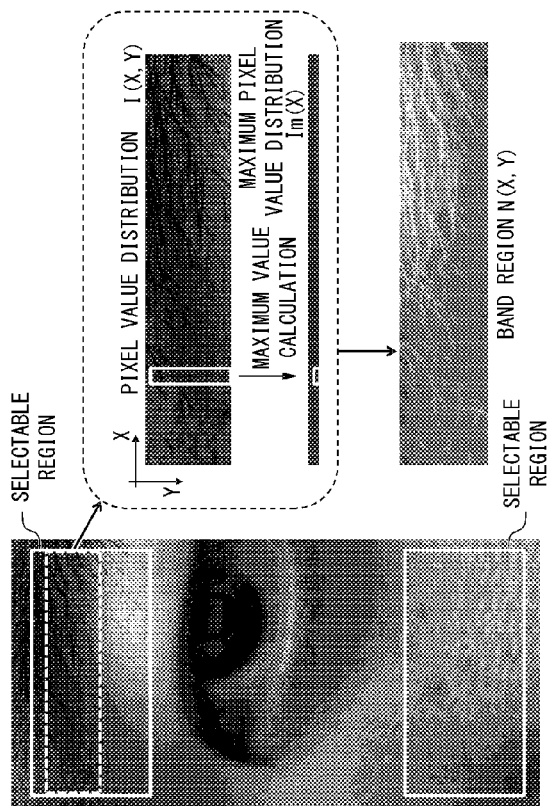
FIGS. 5A and 5B are explanatory drawings illustrating a patch selecting step.
Figure 5A:
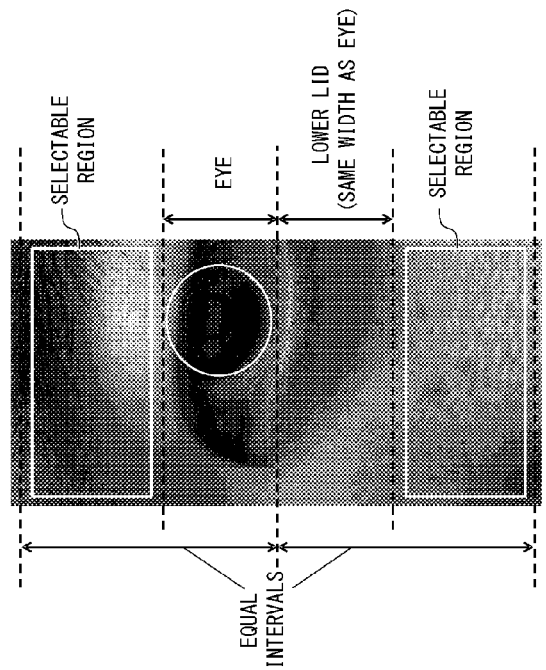

In a band region extracting step S534, a horizontally extended region (hereinafter referred to as a band region) is extracted from a selectable region for each of the cameras, and then the pixel values are normalized (FIG. 5B). The normalization of the pixel values is processing for bringing the intensity of reflected light from a subject surface close to a value independent of the direction of the optical axis of the camera. Specifically, a controller (processing unit) 1153, which will be described later, normalizes the pixel values in the band regions of the first image data and the second image data that are captured by the cameras. For example, normalization according to the following Formula 2 obtains the approximate values of pigment concentrations on the subject surface, achieving a numeric value less dependent upon the direction of the optical axis of the camera.

$$N(x, y) = -\log_{10} \frac{I(x, y)}{I_m(x)} \quad \text{(Formula 2)}$$

where I(x,y) is a pixel value distribution before normalization, N(x,y) is a pixel value distribution after normalization, $I_m(x)$ is the distribution of maximum pixel values at the x coordinates of I(x,y). The maximum pixel value distribution $I_m(x)$ is ideally a gradual distribution like illumination light but may vibrate due to the influence of noise dependent upon the selectable region. In this case, vibrations may be reduced by a low-pass filter and low-order polynomial fitting that are used to suppress noise. The length of the band region in the short-side direction (a width in y-axis direction) is optionally selectable. However, if the subject surface included in the band region changes its tilt angle, the approximation accuracy of Formula 2 decreases. Thus, the length in the short-side direction is desirably reduced such that the change of the tilt angle becomes negligible.

In a mean parallax calculating step S535, a mean parallax between band regions is calculated based on band regions obtained for the respective cameras. First, a subject part (e.g., a part around an eye) simultaneously imaged by two cameras will be described below. Hereinafter, band regions for the two cameras are distinguished from each other as band regions 1 and 2. The band region 2 is further divided into left and right band regions referred to as 2A and 2B. The long sides of the band regions 2A and 2B do not need to be strictly half that of the band region 2. If the band region 2 includes a sharply tilted part, e.g., a nose side or a background other than the subject or a head coil, the lengths of the long sides may be adjusted.

After the band region 2 is divided, the correlation between a band region 1 and the band region 2A and the correlation between the band region 1 and the band region 2B are computed, and then a peak height and a peak position are calculated from the correlation distributions. The correlations are determined by the following Formula 3.

$$\text{correlation}(I_1, I_t) = \text{abs}(F^{-1}(F(I_1) \cdot \text{conj}(F(I_t)))) \quad \text{(Formula 3)}$$

where $I_1$ and $I_t$ are the pixel value distributions of a band region 1 and a band region t (t=2A or 2B), F and $F^{-1}$ are Fourier transform and inverse Fourier transform, conj is a function for returning a complex conjugate distribution, and abs is a function for returning an absolute value distribution. Fourier transform may be two-dimensional or one-dimensional in the long-side direction. The correlation computation may be replaced with an operation that can estimate the position of the band region 2A (or the band region 2B) in the band region 1 with reliability (equivalent to the peak height). For example, phase correlation or template matching can be used. However, in the case of a real-space operation such as template matching, it is necessary to read "the peak height of the correlation distribution" as "the similarity of a template" and "peak position" as "a position having high template similarity".

After the peak height and the peak position of the correlation distribution are calculated, the band region with a higher peak is selected (tentatively referred to as a band region P). The mean parallax, which is an output value in the mean parallax calculating step S535, is a difference between the peak position of the band region P and the center position of the band region P in the band region 2.

If a subject part is simultaneously imaged by three or more cameras (N cameras), the process of selecting two of the N cameras and performing the mean parallax calculating step S535 for the two cameras may be repeated. However, the direction of a parallax may be different from the long-side direction of the band region depending upon the layout of the cameras. In this case, it is necessary to avoid a combination of the cameras or calculate band regions in different directions in advance in the band region extracting step S534.

In a patch parallax calculating step S536, patch candidates are selected from the band region, and then a parallax is calculated for each patch candidate. As in the description of the mean parallax calculating step S535, a subject part simultaneously imaged by two cameras will be first described below. Band regions for the two cameras are distinguished from each other as band regions 1 and 2 (or a first image and a second image).

Figure 6:
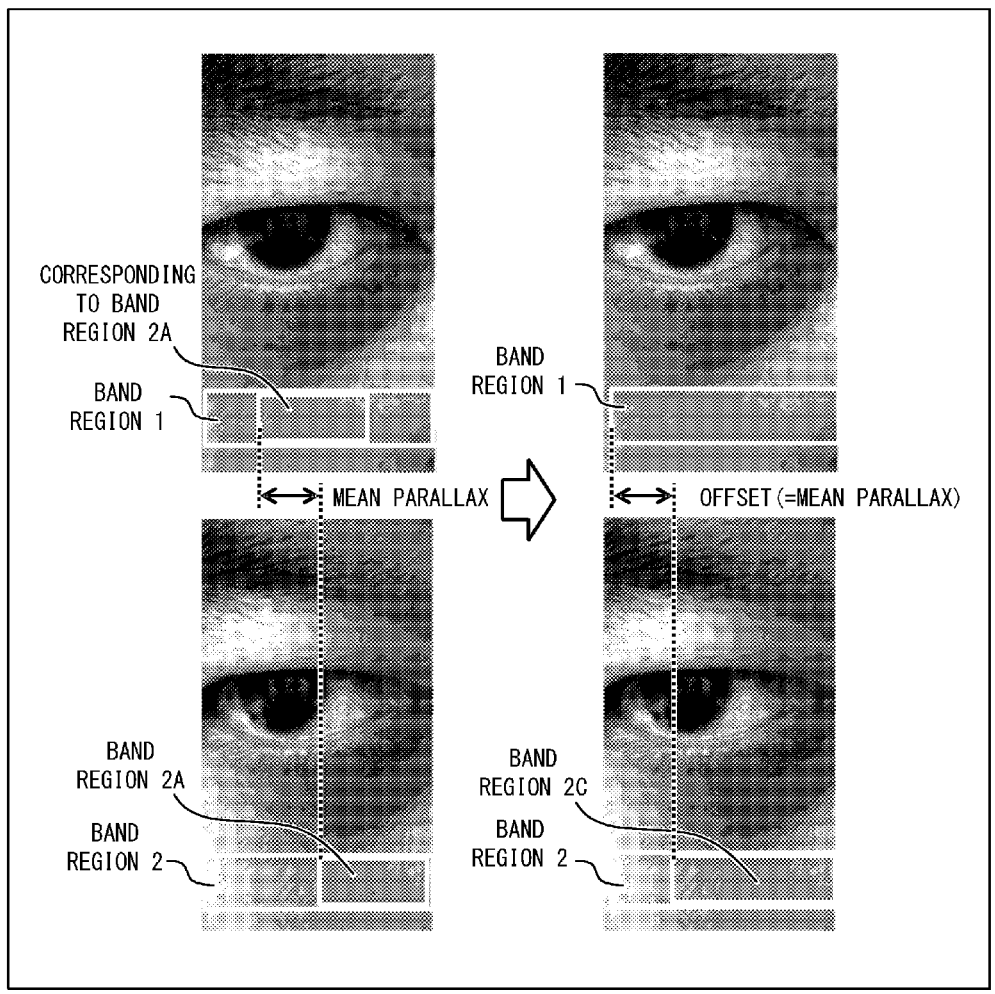
FIG. 6 is an explanatory drawing illustrating the patch selecting step.

First, a region including the same subject in the band region 1 and the band region 2 is calculated based on the mean parallax determined in the mean parallax calculating step S535. For example, in the relationship between the band regions 1 and 2 and the mean parallax on the left side of FIG. 6, a region (hereinafter referred to as a band region 2C) obtained by removing an offset equivalent to the mean parallax from the band region 2 includes the same subject part as the band region 1.

After the band region 2C is selected, a plurality of patch candidates (small region candidates) are selected from the band region 2C. Extremely large patch candidates may increase a computation time in the patch tracking step S512 when a head motion is measured. Patch candidates are preferably squares as large as the length of the band region in the short-side direction.

After the patch candidates are obtained, the correlation between the band region 1 and each of the patch candidates is computed (Formula 3), and then a peak height and a peak position are calculated from the correlation distributions. As in the mean parallax calculating step S535, the correlation computation may be replaced with phase correlation or template matching. A difference between the peak position and the position of the patch candidate in the band region 2 is denoted as a parallax for each of the patch candidates.

Figure 7:
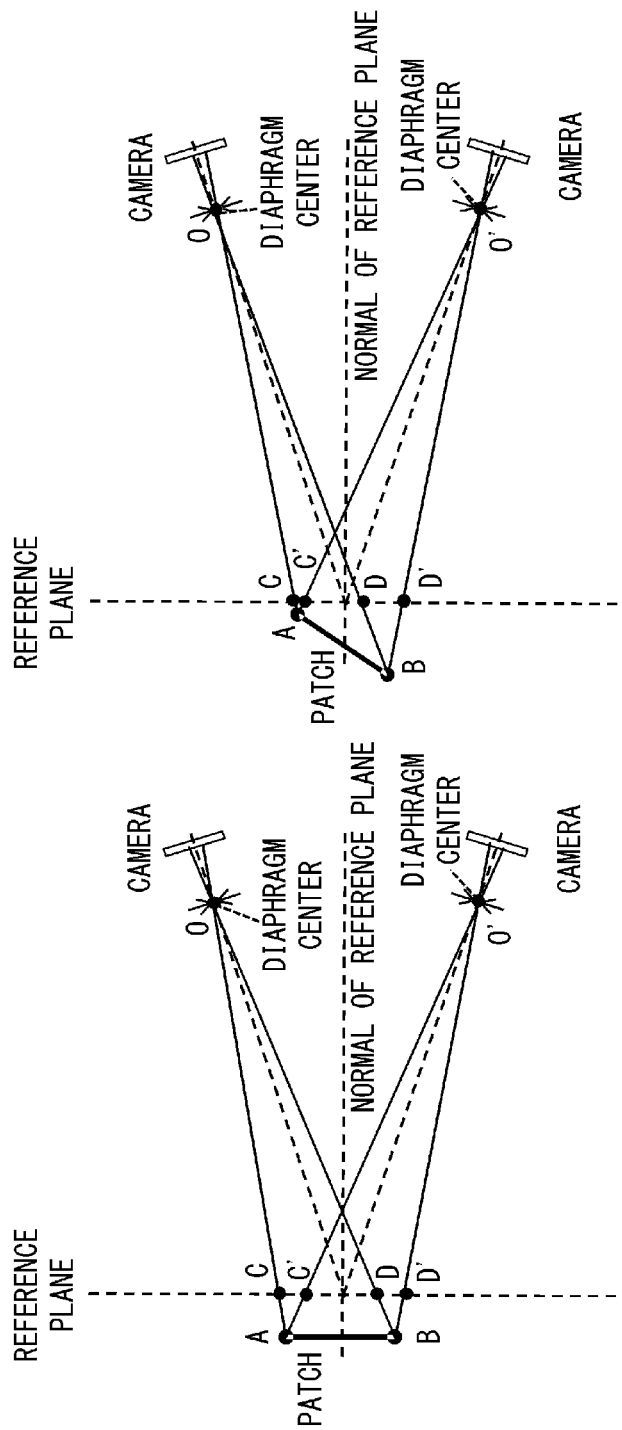
FIGS. 7A and 7B are explanatory drawings illustrating the relationship between the orientation of a patch candidate and the reduction ratio of a patch candidate image.

A parallax calculated for each of the patch candidates may be a false value generated by false recognition of a texture pattern. This requires the removal of patch candidates with incorrect parallaxes. The correctness of a parallax for each of the patch candidates (hereinafter referred to as parallax reliability) is associated with the normal of the subject surface having the patch candidates (hereinafter referred to as a patch candidate normal). The parallax reliability will be described based on the relationship between the orientation of the patch candidate and the reduction ratio of a patch candidate image included in the reference plane data (FIGS. 7A and 7B). In the calculation of the patch candidate image included in the reference plane data, two straight lines AO and BO passing through two points A and B, which correspond to two sides of the patch candidate, and a diaphragm center O are determined, and intersection points C and D of the two straight lines AO and BO and a reference plane are determined. A line segment CD corresponds to the patch candidate image included in the reference plane data. The reduction ratio of the patch candidate image is the ratio of the length of the line segment CD to the size of the patch candidate (the length of a line segment AB).

If the direction of the normal of the patch candidate and the normal of the reference plane agree with each other (FIG. 7A), the cameras have equal reduction ratios, so that patch candidate images (line segments CD and C'D') calculated for the respective cameras agree with each other. If the direction of the normal of the patch candidate and the normal of the reference plane do not agree with each other (FIG. 7B), a difference in reduction ratio appears, so that patch candidate images calculated for the respective cameras do not agree with each other.

If the cameras have different patch candidate images, the height of a correlation peak between the band region 1 and the patch candidate decreases, which may increase the possibility of erroneous detection of second and third peaks. For this reason, if the direction of the normal of the patch candidate and the normal of the reference plane do not agree with each other, the parallax reliability may decrease.

In the present embodiment, patch candidates with high parallax reliability are selected with respect to multiple peaks in the autocorrelation distribution of patch candidate images included in the reference plane data and the mean parallax determined in the mean parallax calculating step S535. The autocorrelation distribution is a correlation distribution when $I_1$ and $I_t$ in Formula 3 are the pixel value distributions of patch candidate images included in the reference plane data. Ideally, the peak height of a patch candidate with high parallax reliability has a value close to the peak height of the autocorrelation distribution. If the autocorrelation distribution has a second highest peak close to the first peak, the second peak may be used for detecting a parallax. This may generate a false parallax. Thus, the ratio of the heights of the first and second peaks also serves as a criterion of parallax reliability.

The reason why the mean parallax can be used as the second criterion will be described below. A surface profile around an eye has a small height difference, and the subject surface has many points parallel to a plane (reference plane) approximating the subject surface in a plane. Hence, the mean parallax determined for the band region approximates the parallax of a point parallel to the reference plane. Since a patch candidate parallel to the reference plane has high parallax reliability, the mean parallax can be used as a criterion.

In the selection of a patch candidate with high parallax reliability, for example, three-step screening can be performed. First, first screening is performed such that the height of a correlation peak between the band region 1 and a patch candidate is at least 50% of the peak height of the autocorrelation distribution. In second screening, a patch candidate is selected such that the height of the second peak is less than 70% of the first peak of the autocorrelation distribution. In third screening, a patch candidate close to the mean parallax is selected. If specific screening does not function, the three-step processing may be partially omitted. If template matching is used without correlation computation, a value such as the degree of coincidence of templates may be used instead of an autocorrelation peak. Specifically, multiple regions are respectively set for the images of frames obtained by the cameras, and some regions to be used as patches are selected based on the reliability of the patches.

If a subject part is simultaneously imaged by three or more cameras (N cameras), the process of selecting two of the N cameras and performing the patch parallax calculating step S536 for the two cameras may be repeated as in the mean parallax calculating step S535.

In a patch number determination S537, it is determined whether a predetermined number of patch candidates has been obtained. If the predetermined number of patch candidates has not been obtained, a band region at a different position is calculated in the band region extracting step S534, and the number of patches is increased. In this way, in the patch selecting step S511, a plurality of patches to be tracked can be selected.

<Patch Tracking Step of the Tracking Step>

Figure 4B:
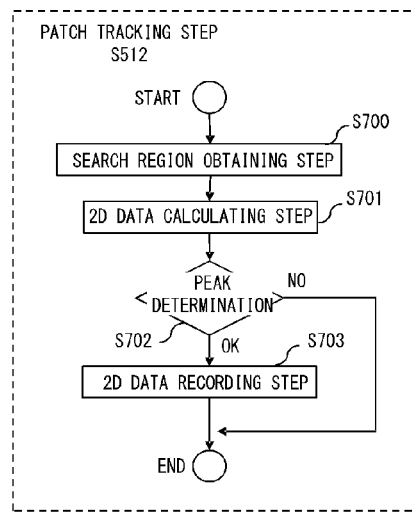

Referring to FIG. 4B, an example of the process of the patch tracking step S512 will be described below. In a search region obtaining step S700, reference-plane image data is created for additionally obtained movie frame, and a pixel section (hereinafter referred to as a search region) that may include patches is obtained. The center coordinate of the search region is estimated based on center coordinate data (hereinafter referred to as 2D data) on a patch at a shooting time before the current time. For example, if 2D data on a patch is $x_1$ and $x_2$ at past shooting times $t_1$ and $t_2$, a center coordinate $x_3$ of the search region at the current time $t_3$ can be calculated by the following Formula 4.

$$x_3 = x_1 + \frac{t_3 - t_1}{t_2 - t_1}(x_2 - x_1) \qquad \text{(Formula 4)}$$

The search region may have any size larger than the patch. The maximum moving distance of the patch is preferably added to the size of the patch. Multiple search regions may be obtained for each patch or a large search region may be selected for multiple patches.

In a 2D data generating step S701, 2D data on the patch in the movie frame at the current time $t_3$ is generated based on the search region obtained in the search region obtaining step S700 and the correlation computation (Formula 3) with the patch. In Formula 3, $I_1$ is the search region and $I_t$ is the patch. Pixels may be normalized as in Formula 2 or patches may be enhanced. Determination of the position of the patch in the search region based on a peak in the correlation distribution is the same processing as in the patch selecting step S511. 2D data on the patch in the movie frame at the current time $t_3$ is a value obtained by adding the center coordinate value of the search region to the position of the patch in the search region. As in the patch selecting step S511, the correlation computation may be replaced with phase correlation or template matching.

The obtained 2D data on the patch in the 2D data generating step S701 may be a false value obtained by the influence of false recognition of a texture. In peak determination S702, the correctness of the 2D data on the patch is determined based on the peak height of the autocorrelation distribution of the patch. The peak height of the autocorrelation distribution can be used as a criterion for the same reason as the determination of parallax reliability in the patch parallax calculating step S536 of the patch selecting step S511.

If it is determined that the 2D data on the patch is correct in the peak determining step S702, the 2D data is recorded in an array in a 2D data recording step S703. If 2D data on a patch is not obtained in the movie frame at the current time $t_3$, a 2D-data estimated value is calculated in a failed-patch estimating step S517, which will be described later. The 2D data recorded in the array and the 2D-data estimated value are used for estimating the center coordinate of the search region in the search region obtaining step S700. In this way, the patch tracking step S512 can obtain two-dimensional coordinate data on the destinations of patches (that is, the two-dimensional coordinates of patches in the movie frame at the current time).

<3D Tracking Step of the Tracking Step>

Figure 4C:
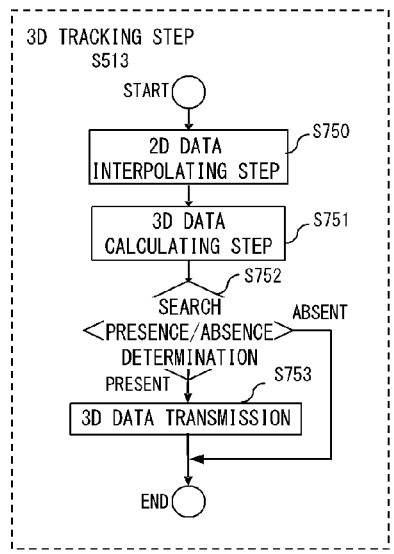

Referring to FIG. 4C, an example of the process of the 3D tracking step S513 will be described below. In a 2D data interpolating step S750, if the shooting time of each camera is slightly deviated, 2D data at the same shooting time is generated by interpolation. An example of 2D data (FIG. 8) recorded in the array in the patch tracking step S512 is used in the following description. In the array, 2D data on five cameras (referred to as cameras A, B, C, D, and E) at eight shooting times ($t_1$, $t_1$+a, $t_1$+b, $t_1$+c, $t_2$, $t_2$+a, $t_2$+b, $t_2$+c) is recorded. a and b are shooting-time offsets for the cameras B and C, respectively, and c is a shooting-time offset shared by the cameras D and E. The offsets are shorter than a time interval between $t_1$ and $t_2$. A hyphen in the 2D data indicates failed acquisition of 2D data in the patch tracking step S512. The cameras A and B capture images of a part around a right eye, whereas the cameras C, D, and E capture images of a part around a left eye. Right-eye and left-eye regions each include four patches.

The generation of 2D data at time $t_2$ will be described below. Since the shooting times vary among the cameras, 2D data other than the camera A is not obtained. The 2D data other than the camera A is generated by interpolation (Formula 5) when 2D data $x_{bef}$ and $x_{aft}$ are obtained at times (referred to as $t_{bef}$ and $t_t$) around time $t_2$.

$$x_{cur} = x_{bef} + \frac{t_{cur} - t_{bef}}{t_{aft} - t_{bef}}(x_{aft} - v_{bef}) \qquad \text{(Formula 5)}$$

where $t_{cur}$, corresponds to time $t_2$, and $x_{cur}$ is 2D data at time $t_2$. For example, 2D data ($x_{cur}$) on the camera B at time $t_2$ is generated from 2D data ($x_{bef}$) on the camera B at time $t_1$+a and 2D data ($x_t$) on the camera B at time $t_2$+a. According to the interpolation, at least two pieces of 2D data from the camera A and the camera B can be obtained for patches 1 and 3, respectively. Thus, three-dimensional coordinate data on the patches can be generated in a subsequent 3D data generating step S751. The patches of a left eye are similarly interpolated, so that at least two pieces of 2D data at the same time can be obtained for patches 6 and 7.

In the example of FIG. 8, 2D data is generated at a time common to the cameras A, B, C, D, and E. For example, 2D data on the cameras A and B may be generated at time $t_2$, and 2D data on the cameras C, D, and E may be generated at time $t_2$+1). If different times are set for the sets of cameras, it is necessary to determine values at the same shooting time by interpolation in the subsequent 3D data generating step S751. If the subject slowly moves and motions are negligible in the shooting-time offsets a, b, and c, 2D data at the closest time to $t_2$ may be used instead.

In the 3D data generating step S751, three-dimensional coordinate data (hereinafter referred to as 3D data) on patches is generated based on 2D data obtained in the 2D data interpolating step S750. For example, if two pieces of 2D data are obtained for one patch, 3D data P can be generated using the following Formula 6.

$$P = \frac{\sum_{i=1}^{2}(\alpha_i \cdot (X_i - U_i) + X_i)}{2}, \qquad \text{(Formula 6)}$$

$$\begin{pmatrix} \alpha_1 \\ \alpha_2 \end{pmatrix} = pinv([X_1 - U_1 \quad -X_2 + U_2]) \cdot (X_2 - X_1)$$

where $X_1$ and $X_2$ are three-dimensional coordinate data obtained by adding 0 as a three-dimensional element to two pieces of 2D data, $U_1$ and $U_2$ are three-dimensional coordinate data on the diaphragm center determined in the calibration step S510, $\alpha_1$ and $\alpha_2$ are parameters, and pinv(A) is a pseudo inverse matrix for a matrix A.

A technique (a method of least squares using a pseudo inverse matrix) used in Formula 6 is robust against an error included in 2D data but has a heavy computation load. If any error is not included, simplified processing may be used to determine an intersection point of two light beams from the three-dimensional coordinate data $X_1$ and $X_2$ during the backtrace of the light beams. If three or more (denoted as N) pieces of 2D data are obtained for one patch, the process of selecting two of N and determining 3D data according to Formula 6 is repeated, thereby calculating the mean value of the obtained pieces of 3D data. The obtained 3D data is recorded in an array.

In search presence/absence determination S752, it is determined whether 3D data is being searched for. If 3D data is being searched for, the recorded 3D data is transmitted. In this way, the 3D tracking step S513 allows the generation of 3D data on patches.

<Subject Motion Calculating Step of the Tracking Step>

Figure 4D:
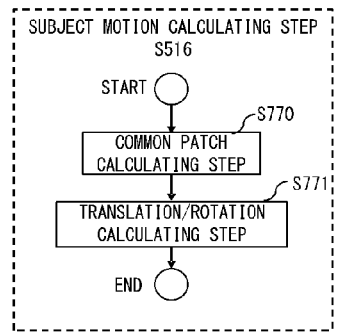

Referring to FIG. 4D, an example of the process of the subject motion calculating step S516 will be described below. In a common patch calculating step S770, the numbers (k=1, 2, . . . N) of the common patches of the reference coordinate data and the 3D data (shooting time T) recorded in the array in the 3D tracking step S513.

In a translation/rotation generating step S771, the translation/rotation of the subject at shooting time T is generated by using the reference coordinate data and the 3D data that correspond to the patch numbers determined in the common patch generating step S770. The translation/rotation is determined so as to minimize a skin motion distance f expressed by the following Formula 7.

$$f(s, \theta; X_{o1}, \cdots X_{oN}, X_{c1}, \cdots X_{cN}) = \qquad \text{(Formula 7)}$$

$$\sum_{k=1}^{N} ssd(R(\theta) \cdot X_{ok} + s, X_{ck})$$

where s is the translation vector of the subject at shooting time T and $\theta$ is a rotation vector with a three-axis rotation angle serving as an element. $X_{ok}$ is reference coordinate data on the k-th patch $X_{ck}$ is 3D data at shooting time T. $R(\theta)$ is a function for returning a rotation matrix to the rotation vector $\theta$, and ssd(p,q) is a function for returning the root sum square of a difference between the elements of three-dimensional vectors p and q.

When the skin motion distance reaches a minimum value $\theta$, the translation/rotation of the subject has the highest accuracy. The translation/rotation obtained in the subject motion calculating step S516 is used as an approximate value having low accuracy. In this way, the subject motion calculating step S516 allows the calculation of the approximate value of translation/rotation serving as subject motion data.

<Failed-Patch Estimating Step of the Tracking Step>

Figure 4E:
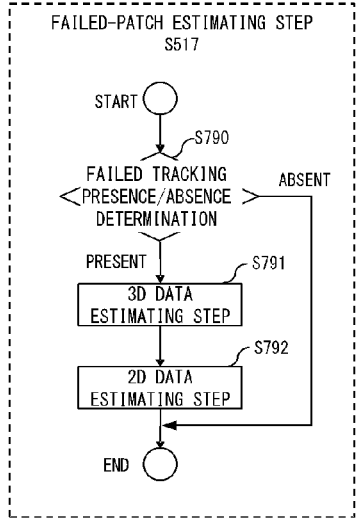

Referring to FIG. 4E, an example of the process of the failed-patch estimating step S517 will be described below. In failed tracking presence/absence determination S790, the 2D data recorded in the matrix in the patch tracking step S512 is examined to determine the presence or absence of a patch where 2D data is not recorded (hereinafter referred to as a failed patch). If a failed patch is confirmed, a 3D data estimating step S791 is performed.

In the 3D data estimating step S791, 3D data on the failed patch is estimated by using the following Formula 8.

$$X'_{cm} = R(\theta) \cdot X_{om} + s \quad \text{(Formula 8)}$$

where m is the number of the failed patch. $X'_{cm}$ is a 3D data estimated value of the failed patch, and $X_{om}$ is the reference coordinate data corresponding to the failed patch. s and θ are the translation vector and the rotation vector that are determined in the subject motion calculating step S516, and R(θ) is the function for returning the rotation matrix to the rotation vector θ.

In this formula, the $X'_{cm}$ on the failed patch is estimated based the reference coordinate data $X_{om}$. Formula 9 may be used based on 3D data $X_{bm}$ at a shooting time (denoted as $T_{bef}$) immediately before the current shooting time T.

$$X'_{cm} = R(\theta) \cdot R(\theta')^{-1} \cdot (X_{bm} - s') + s \quad \text{(Formula 9)}$$

where s' and θ' are a translation vector and a rotation vector that are determined at the shooting time $T_{bef}$ in the subject motion calculating step S516. The 3D data at the shooting time $T_{bef}$ includes a skin motion near the shooting time T, thereby obtaining an estimated value with high accuracy.

After the same processing as in the subject motion calculating step S516 is performed using the 3D data at the shooting time $T_{bef}$ as second reference coordinate data, Formula 8 may be used based on the second reference coordinate data, though the computation load increases. An estimated value is more accurately obtained than in Formula 9.

In a 2D data estimating step S792, 2D data in the reference-plane image data for each camera is estimated by using the following Formula 10.

$$x'_{cmi} = \frac{x'_{cm} + \beta_i \cdot u_i}{\beta_i + 1}, \beta_i = -\frac{X'^{(3)}_{cm}}{U^{(3)}_i} \quad \text{(Formula 10)}$$

where $x'_{cmi}$ is the 2D estimated value of a failed patch corresponding to the i-th camera, and $x'_{cm}$ is a vector including the first and second elements of the 3D data estimated value $X'_{cm}$ of the failed patch as components. $U_i$ is a vector including the first and second elements of a diaphragm center coordinate $U_i$ of the i-th camera as components. $X'^{(3)}_{cm}$ and $U^{(3)}_i$ are the third element of $X'_{cm}$ and $U_i$. In this way, the failed-patch estimating step S517 allows the estimation of the two-dimensional coordinates of a patch moved out of the movie frame or a patch failed to be calculated in the patch tracking step S512.

<Flow of Overall Skin (Subject)-Motion Data Creating Step>

Referring to FIG. 3B, an example of the process of a skin-motion data creating step will be described below. In a grouping step S810, 3D data is obtained from the tracking process, and then the obtained 3D data is divided into groups on the basis of the skin motion distance f (Formula 7). In an intragroup structuring step S811, 3D data representing the group is selected, and a translation/rotation parameter from the representing 3D data to group members is calculated.

In an optimizing step S812, a translation/rotation parameter between the reference coordinate data and the representing 3D data is calculated by optimization. Subsequently, the main component vector of the skin (subject) motion data may be calculated based on the translation/rotation parameters obtained in the intragroup structuring step S811 and the optimizing step S812.

In skin-motion data transmission S813, the skin motion data or the main component vector of the skin motion data is transmitted to the tracking process. The processing of the skin-motion data creating step corresponds to processing for evaluating, according to the skin motion distance f of Formula 7, the similarity of three-dimensional positional relationships among a plurality of small regions (patches) set on the surface of the subject, and classifying local motions (skin (subject) motions) according to the similarity.

<Grouping Step of the Skin-Motion Data Creating Step>

Figure 9A:
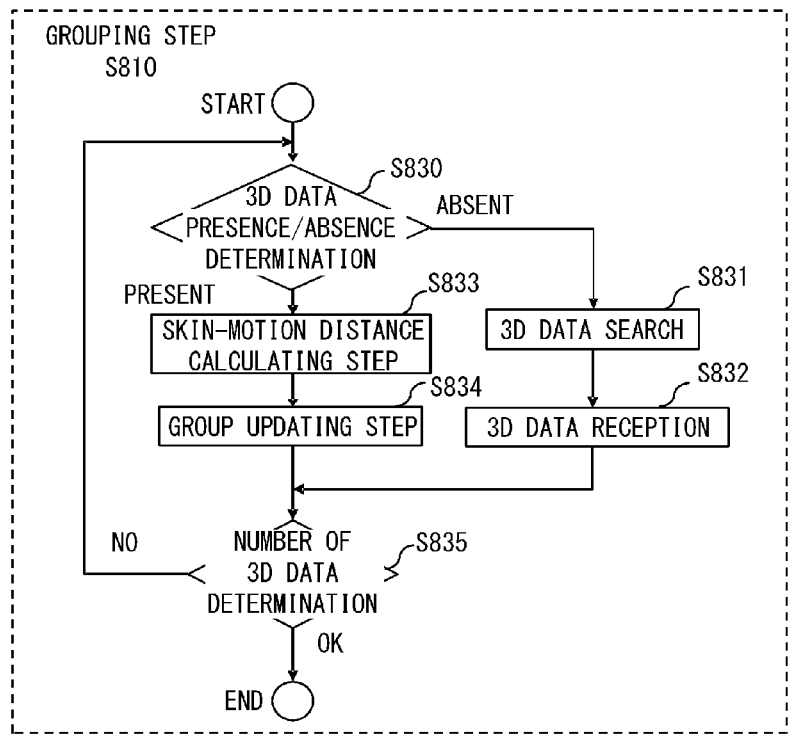
FIGS. 9A to 9C are flowcharts indicating an example of the process of the skin-motion data creating step.

Referring to FIG. 9A, an example of the process of the grouping step S810 will be described below. In 3D data presence/absence determination S830, the presence or absence of 3D data not belonging to a group is determined for 3D data obtained in the tracking process. In the absence of 3D data not belonging to a group, new 3D data is obtained in 3D data search S831 and 3D data reception S832. In the presence of 3D data not belonging to a group (hereinafter independent 3D data), a skin-motion distance calculating step S833 is performed.

In the skin-motion distance calculating step S833, a skin motion distance f (Formula 7) between the independent 3D data and a group member (3D data) in each group is calculated. The minimum value of the skin motion distance f may be calculated by substituting the independent 3D data and the 3D data on the group member into $X_{ok}$ and $X_{ck}$, respectively, in Formula 7. This calculates the skin motion distance of independent 3D data for each group. If no group is created at S833, the processing of S833 may be skipped.

In a group updating step S834, a group for which a minimum skin motion distance is calculated in S833 is selected as a candidate group. The skin motion distance for the candidate group is compared with a predetermined threshold. If the skin motion distance is smaller than the threshold, the independent 3D data is registered in the corresponding candidate group. If the skin motion distance for the candidate group is equal to or larger than the threshold, it is assumed that any group close to the independent 3D data is not present. A new group is generated, and the independent 3D data is registered in the new group. If the processing of S833 is skipped (no group is present), a new group may be generated to register the independent 3D data therein. In 3D data number determination S835, the number of pieces of grouped 3D data is determined. When at least a certain number of pieces of 3D data are grouped, the grouping step S810 is completed.

Figure 10A:
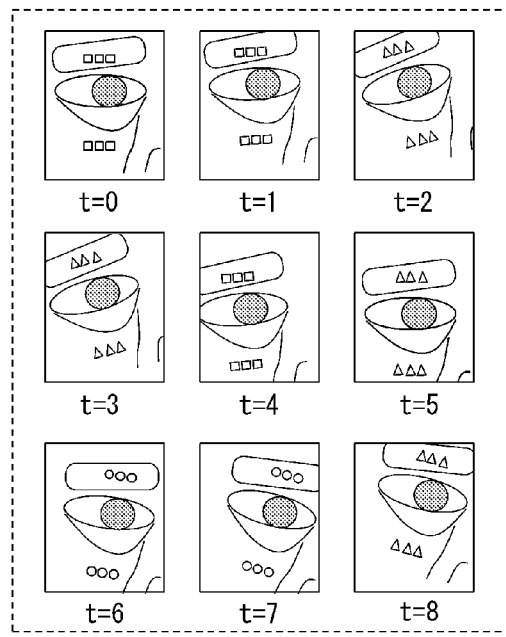
FIGS. 10A and 10B are explanatory drawings illustrating the effect of a grouping step.
Figure 10B:
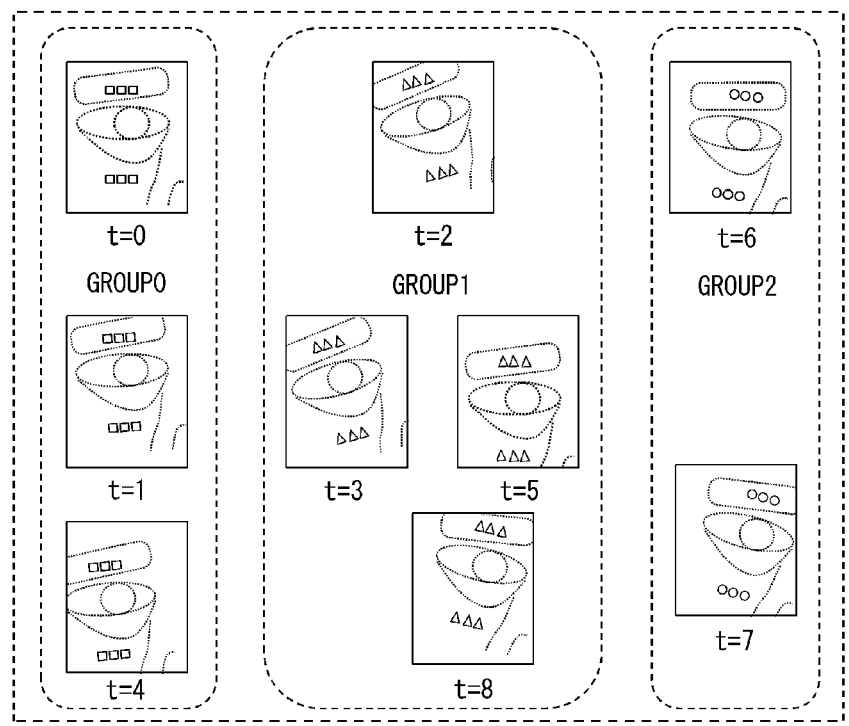

The effect of the grouping step S810 will be described below according to the layout of patches (FIGS. 10A and 10B). The 3D data obtained from the tracking process corresponds to patches (pixel sections indicated by circular, triangular, and square markers in FIG. 10A) included in movie frames at shooting times t=0, 1, . . . 8. The markers represent patch layout variations due to skin motions. After the grouping step S810 is applied, the movie frames (3D data) at shooting times t=0, 1, . . . 8 are grouped with reference to patch layout variations (circular, triangular, and square markers) due to skin motions (FIG. 10B). In this way, the grouping step S810 can obtain a plurality of groups of 3D data including similar-sized skin motions.

<Intragroup Structuring Step of the Skin-Motion Data Creating Step>

Figure 9B:
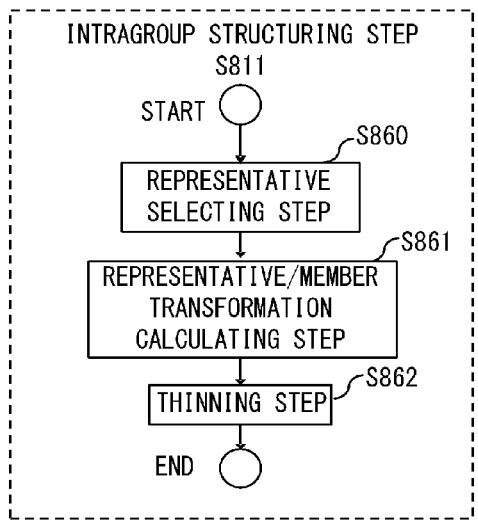

Referring to FIG. 9B, an example of the process of the intragroup structuring step S811 will be described below. In a representative selecting step S860, 3D data representing each group is selected. One of the group members may be selected or coordinate transformation (translation/rotation) may be performed to select the mean value of the group member having a minimum skin motion distance. Alternatively, as in clustering (e.g., K-means), the member may be replaced with another so as to reduce a skin motion distance from the representative of a new group.

In a representative/member transformation calculating step S861, a transformation (translation/rotation parameter) from the group representative to each group member is calculated. For example, 3D data on the group representative and group members is substituted into $X_{ok}$ and $X_{ck}$, respectively, in Formula 7, and the translation/rotation parameter for minimizing the skin motion distance f is used.

In a thinning step S862, a group including an extremely small number of group members as compared with other groups is deleted. Such a group is likely to be generated by an error included in 3D data, causing an error in the measurement of a subject motion.

If the group member used for calculation in the skin-motion distance calculating step S833 is used as a group representative, the representative selecting step S860 may be omitted. Likewise, the representative/member transformation calculating step S861 can be omitted by using, in the skin-motion distance calculating step S833, the translation/rotation parameter obtained in the calculation of the skin motion distance (Formula 7).

Figure 11:
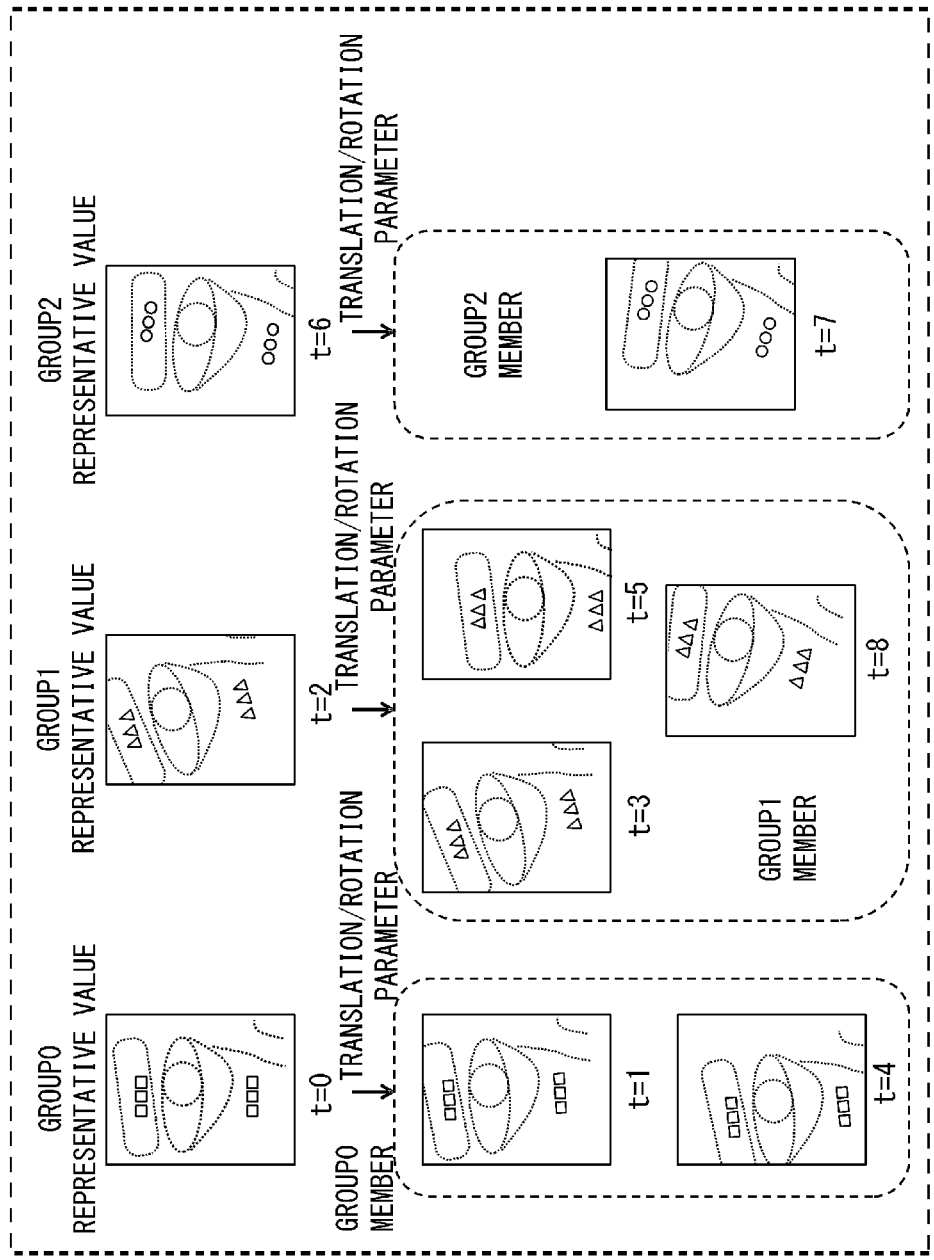
FIG. 11 is an explanatory drawing illustrating the effect of an intragroup structuring step.

Referring to FIG. 11, the effect of the intragroup structuring step S811 will be described below. In the representative selecting step S860, 3D data at shooting time t=0, 2, 6 is selected as a representative for three groups. Since the members of each group are provided in a patch layout where the group representative is translated and rotated, the translation/rotation parameter is obtained by the representative/member transformation calculating step S861. In this way, the intragroup structuring step S811 allows the acquisition of the parameter of a coordinate transformation to a group member from 3D data representing each group.

<Optimizing Step of the Skin-Motion Data Creating Step>

Figure 9C:
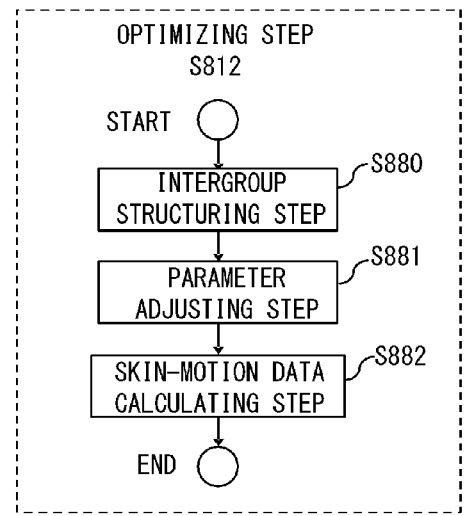

Referring to FIG. 9C, an example of the process of the optimizing step S812 will be described below. In an intergroup structuring step S880, the approximate value of a transformation (translation/rotation parameter) of each group representative to 3D data is calculated from the reference coordinate data selected based on the 3D data. Any 3D data may be selected as the reference coordinate data. If one of group representatives is selected, the calculation of the approximate value of the translation/rotation parameter can be omitted for one group. The approximate value is calculated because a skin motion distance does not approach 0 between 3D data segments included in different groups and thus the translation/rotation parameter cannot be accurately calculated.

In a parameter adjusting step S881, the translation/rotation parameter approximate value obtained in the intergroup structuring step S880 is adjusted so as to minimize an evaluation function φ expressed by the following Formula 11.

$$\phi(s_1, s_2, \cdots, s_M, q_1, q_2, \cdots, q_M) = \sum_{t_a, t_b \in \Omega, |t_a - t_b| < \varepsilon} (\text{diff\_s}(t_a, t_b) + \text{diff\_q}(t_a, t_b))$$ (Formula 11)

where $s_j$ and $q_j$ (j=1, 2, . . . M) are variables corresponding to M translation/rotation parameter approximate values obtained in the intergroup structuring step S880. $s_j$ is a translation vector included in the transformation of the j-th group representative to 3D data, and $q_j$ is a rotation parameter (expressed by a unit quaternion instead of Euler angles or a matrix because the unit quaternion facilitates the calculation). Ω is a set of shooting times for 3D data, and $t_a$ and $t_b$ are two shooting times with a time difference smaller than a predetermined value ε. diff_s and diff_q are functions expressed by Formulas 12 and 13.

$$\text{diff\_s}(t_a, t_b) = ssd(R_L(t_a) \cdot s_{g(t_a)} + S_L(t_a), R_L(t_b) \cdot s_{g(t_b)} + S_L(t_b))$$ (Formula 12)

$$\text{diff\_q}(t_a, t_b) = (1 - |(q_{g(t_a)} \cdot Q_L(t_a)) \cdot (q_{g(t_b)} \cdot Q_L(t_b))|)^2$$ (Formula 13)

where g(t) is a function for returning the number of the group of 3D data at shooting time t. A function ssd(A,B) is a function for returning the root sum square of a difference between the elements of vectors A and B. $R_L(t)$, $S_L(t)$, and $Q_L(t)$ are functions for returning the parameters of coordinate transformation to 3D data at shooting time t from representative 3D data on a group numbered g(t). $R_L(t)$ returns a rotation matrix while $S_L(t)$ returns a translation vector. $Q_L(t)$ returns a unit quaternion representing a rotation.

Figure 12:
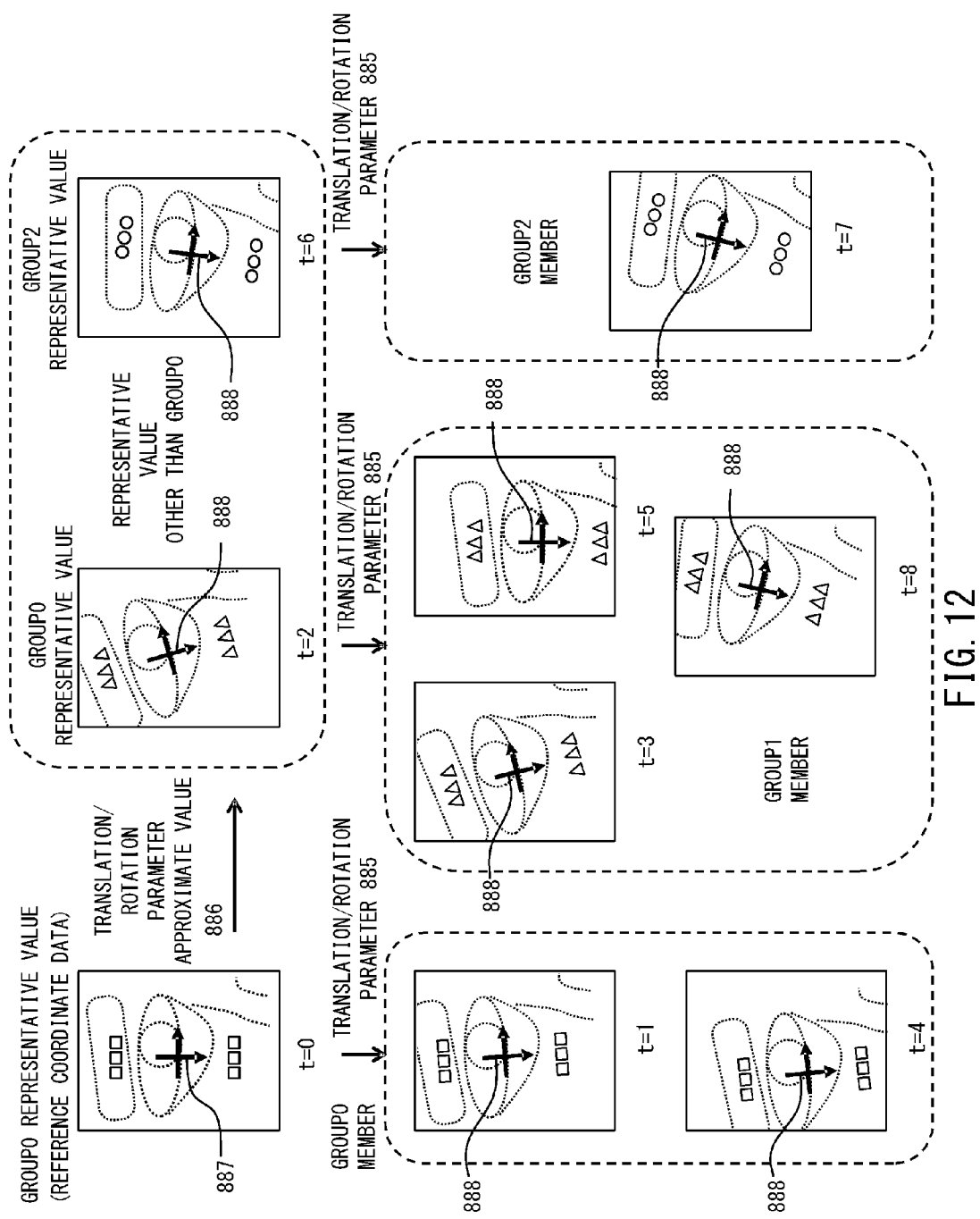
FIG. 12 is an explanatory drawing illustrating the effect of an optimizing step.
Figure 13:
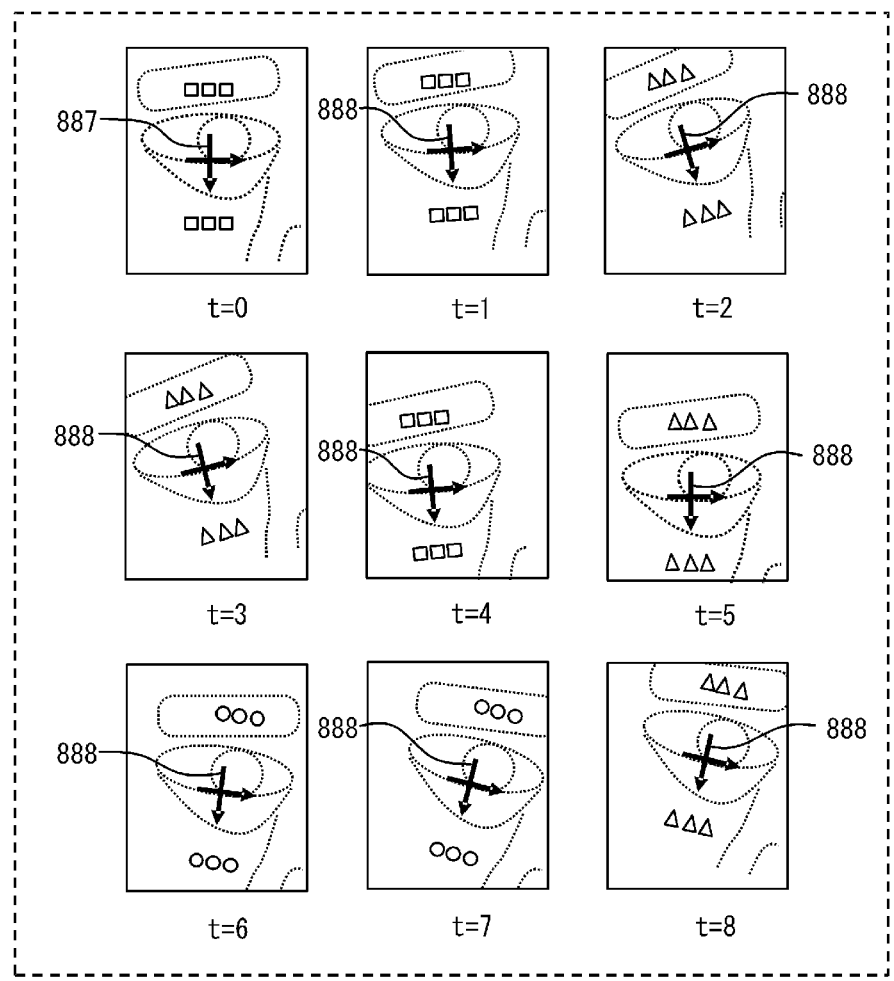
FIG. 13 is an explanatory drawing illustrating the effect of the optimizing step.

The evaluation function φ in Formula 11 is created based on the properties of coordinate transformation with respect to the coordinate axes (hereinafter referred to as reference coordinate axes) of the reference coordinate data. In the following example, the reference coordinate axes are projected into the video frame by using coordinate transformation between pieces of 3D data (FIGS. 12 and 13). In this case, the reference coordinate data is the representative value of group 0. Reference numeral 887 denotes the reference coordinate axis. A translation/rotation parameter 885 is a value obtained by the intragroup structuring step S811 while a translation/rotation parameter approximate value 886 is a value obtained by the intergroup structuring step S880. Coordinate transformation with the translation/rotation parameter 885 and the translation/rotation parameter approximate value 886 obtains a reference coordinate axis 888 after coordinate transformation in each movie frame.

FIG. 13 illustrates the reference coordinate axis 888 arranged in a time sequence after the coordinate transformation of FIG. 12. Thus, when the translation/rotation parameter approximate value 886 is adjusted to a correct value, the origin and direction of the reference coordinate axis 888 are most smoothly changed in a time sequence after the coordinate transformation.

The function diff_s expressed by Formula 12 indicates a difference in the origin coordinates of the reference coordinate axis 888 between adjacent shooting times after the coordinate transformation. The function diff_q expressed by Formula 13 indicates a difference in the three-dimensional rotation of the reference coordinate axis 888 after the coordinate transformation. The evaluation function φ of Formula 11 is the sum of the functions diff_s and diff_q and thus indicates a change of the reference coordinate axis 888 after the coordinate transformation. Thus, in order to minimize the evaluation function φ, a change of the reference coordinate axis 888 in a time sequence is reduced after the coordinate transformation, and the translation/rotation parameter approximate value 886 is adjusted to the correct value. Furthermore, formulas other than Formulas 12 and 13 include indexes indicating the differences of the coordinate origin and the three-dimensional rotation, so that other formulas may be used.

The approximate value of the translation/rotation parameter can be adjusted using various optimization techniques. However, the evaluation function y of Formula 11 is provided in the form of a root sum square with a large number of variables, so that multivariable non-linear least-squares methods such as the Levenberg-Marquardt method are suitably used.

The intergroup structuring step S880 is performed using patches or characteristic points, thereby obtaining the translation/rotation parameter approximate value with high accuracy. In this case, the parameter adjusting step S881 may be omitted.

In a skin-motion data generating step S882, according to the following Formula 14, the inverse transformation of the coordinate transformation from the reference coordinate data to 3D data is determined and 3D data (that is, skin motion data) on the reference coordinate axis 887 is generated.

$$X_{zk}^{(t)} = R_G(g(t))^{-1} \cdot (R_L(t)^{-1} \cdot (X_{ck}^{(t)} - S_L^{(t)}) - s_{g(t)}, k = 1, 2, \ldots, N \quad \text{(Formula 14)}$$

where $X_{ck}^{(t)}$ is 3D data on the k-th patch at shooting time t, and $X_{zk}^{(t)}$ is 3D data converted on the reference coordinate axis 887. $g(t)$, $R_L(t)$, and $S_L(t)$ are the same functions as those introduced in Formula 12, and $R_G(j)$ is a function for returning a rotation matrix included in the transformation from the reference coordinate data to representative 3D data (j-th group).

The shooting time t of the skin motion data $X_{zk}^{(t)}$ can be optionally selected, which requires sampling for all the states of skin motions. For example, shooting times selected for the representative 3D data of all the groups can cover all the states of skin motions.

First Embodiment

Figure 14A:
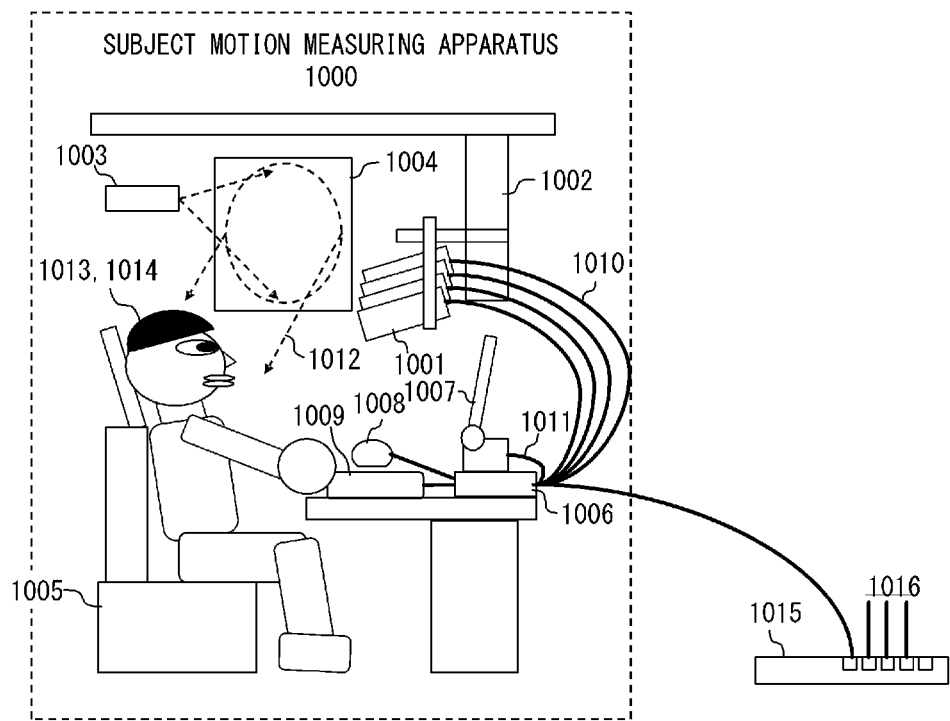
FIGS. 14A and 14B illustrate a configuration example of a subject motion measuring apparatus according to a first embodiment.

Referring to FIG. 14A, a subject motion measuring apparatus 1000 according to a first embodiment of the present invention will be described below. FIG. 14A illustrates an example of the configuration of the subject motion measuring apparatus 1000 according to the first embodiment of the present invention. The subject motion measuring apparatus 1000 according to the present embodiment includes four cameras 1001, a camera-height adjusting stage 1002, a white light source 1003, a reflector 1004, and a chair 1005. Furthermore, the subject motion measuring apparatus 1000 includes a computer 1006, a display 1007, a mouse 1008, a keyboard 1009, network cables 1010, and a display cable 1011. The computer 1006 is connected to a LAN 1016 via a switching hub 1015.

The four cameras 1001 are connected to the computer 1006 via the network cables 1010. The cameras 1001 capture moving image data of one megapixel with a frame rate of 60 fps. The moving image data is transferred to the computer 1006. The cameras 1001 are adjusted to focus on a part around the eyes of a subject 1014 while the back of the head of the subject 1014 is placed on the backrest of the chair 1005. The camera-height adjusting stage 1002 can adjust the heights of the cameras 1001. Moreover, the cameras 1001 are rotated 90° such that movie frames are placed in portrait orientation. The rotations are made to increase a distance between patches in the longitudinal direction (a direction from a nose to a mouth) and improve accuracy in measuring a rotation made by a nod. The white light source 1003 evenly illuminates the reflector 1004, and reflected light 1012 from the reflector 1004 is directed to the head of the subject 1014.

Figure 14B:
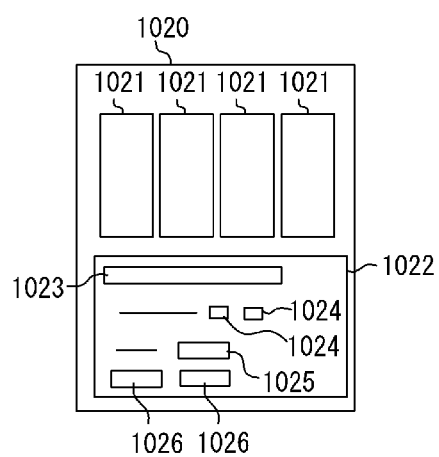

The display 1007 is connected to the computer 1006 via the display cable 1011. FIG. 14B illustrates an example of a display screen 1020 displayed on the display 1007. The display screen 1020 indicates, for example, the states of the cameras 1001 and the contents of computations. For example, moving image display parts 1021, an information display/correction part 1022, a list box 1023, check boxes 1024, edit boxes 1025, and command buttons 1026 can be displayed in the display screen 1020.

<Flow of Processing in the Subject Motion Measuring Apparatus 1000>

Figure 15A:
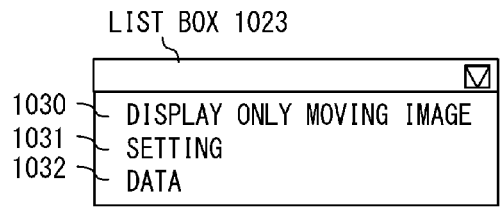
FIGS. 15A and 15B illustrate screen examples of the subject motion measuring apparatus.
Figure 15B:
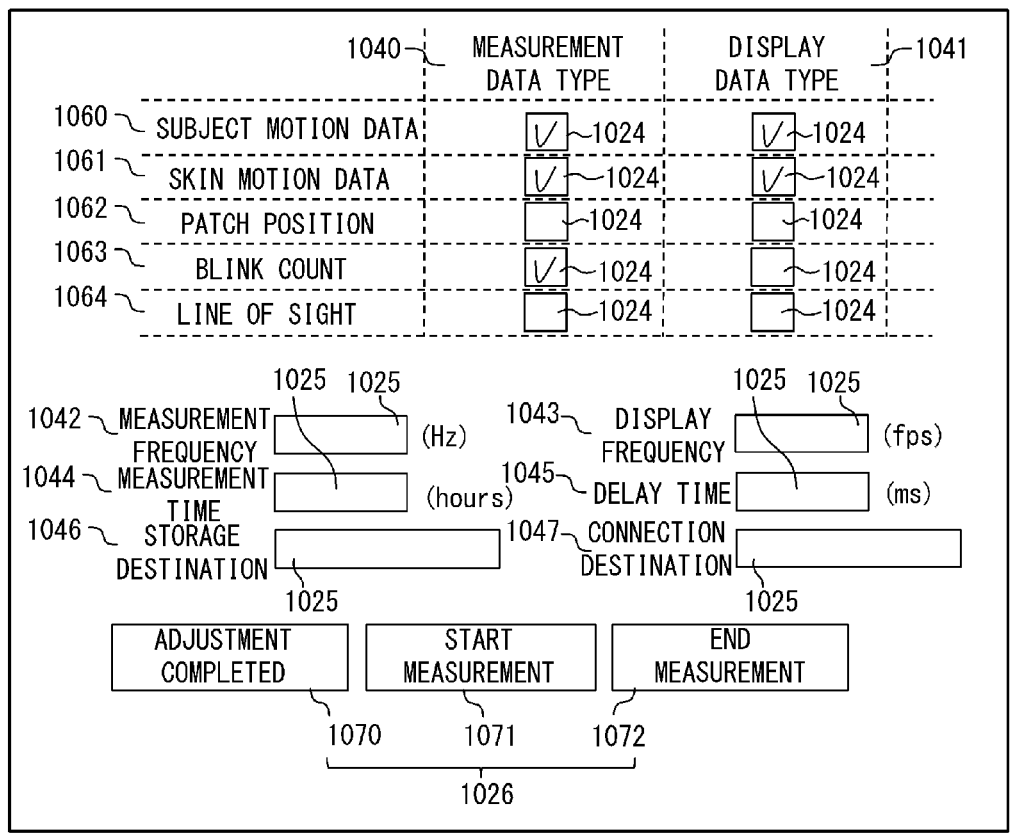

Referring to FIGS. 15A and 15B, the flow of processing performed by the subject motion measuring apparatus 1000 will be described below. An operator 1013 of the subject motion measuring apparatus 1000 first selects a setting 1031, which is an item of the list box 1023, to specify information (hereinafter referred to as a display mode) to be displayed on the moving image display parts 1021 (FIG. 15A). Thus, in the moving image display part 1021, a marker is displayed on a position where an eye is to be located. The operator 1013 instructs the subject 1014 to sit with the head placed on the backrest of the chair 1005 and adjusts the camera-height adjusting stage to project an eye of the subject 1014 near the marker of the moving image display part 1021. After the completion of the adjustment, the operator 1013 inputs the command button 1026 for adjustment completion 1070 (FIG. 15B).

Subsequently, the operator 1013 inputs a measurement data type 1040 and a display data type 1041 by using the check boxes 1024 (FIG. 15B). Moreover, the operator 1013 inputs a measurement frequency 1042, a display frequency 1043, a measurement time 1044, a delay time 1045, a storage destination 1046, and a connection destination 1047 by using the edit boxes 1025 (FIG. 15B). The measurement data type 1040 and the display data type 1041 include subject motion data 1060 (skin motion data 1061), a patch position 1062, a blink count 1063, and a line of sight 1064. After all the items are inputted, the command button 1026 for measurement start 1071 becomes clickable.

When the command button 1026 for the measurement start 1071 is inputted, a tracking process is started in the computer 1006. The subsequent steps are identical to those in a description of the subject motion measuring method.

During the tracking process, data 1032 is selected in the list box 1023 for a display mode (FIG. 15A). Hence, the moving image display part 1021 displays data of a type inputted as the display data type 1041.

Data specified by the measurement data type 1040 is transmitted from the tracking process to the storage destination 1046 and the connection destination 1047 upon obtaining a calculation result. If the delay time 1045 is short, a difference between a shooting time and a time when the calculation result is obtained may exceed the delay time 1045. At this point, data on the shooting time is estimated based on the calculation results of previous shooting times, and then the estimated value is transmitted to the storage destination 1046 and the connection destination 1047.

When the command button 1026 for measurement termination 1072 is inputted, a termination command is transmitted to the tracking process, terminating a measurement.

As described above, the first embodiment of the present invention is a subject motion measuring apparatus capable of measuring a subject motion with high accuracy.

Second Embodiment

Figure 16:
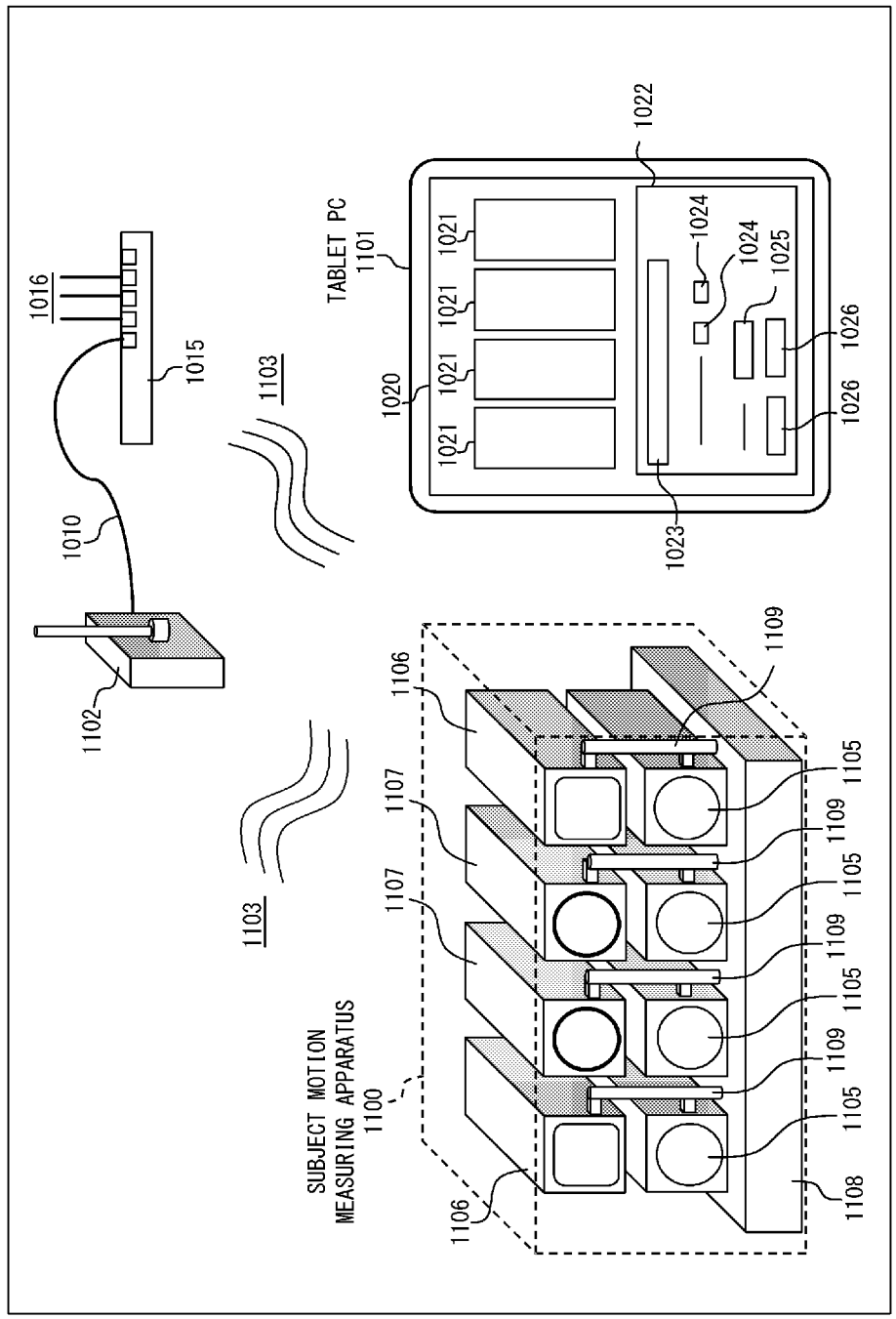
FIG. 16 illustrates a configuration example of the subject motion measuring apparatus according to the first embodiment.

Referring to FIG. 16, a subject motion measuring apparatus 1100 according to a second embodiment of the present invention will be described below. FIG. 16 illustrates an example of the configuration of the subject motion measuring apparatus 1100 according to the second embodiment. The subject motion measuring apparatus 1100 according to the present embodiment achieves higher accuracy, a higher frame rate, and a smaller size as compared with the subject motion measuring apparatus 1000 of the first embodiment. Since the basic configuration is identical to that of the subject motion measuring apparatus 1000, differences will be mainly discussed below.

Functions corresponding to the cameras 1001, the white light source 1003, and the computer 1006 according to the first embodiment are integrated in the subject motion measuring apparatus 1100. Functions such as display and information input are implemented by a tablet PC 1101. Communications between the subject motion measuring apparatus 1100 and the tablet PC 1101 are performed by radio communications 1103. The subject motion measuring apparatus 1100 and the tablet PC 1101 are connected to the LAN 1016 via a wireless router 1102. The subject motion measuring apparatus 1100 is used in front of the face of the subject 1014 (may be mounted on a support mechanism, for example, the camera-height adjusting stage 1002 of FIG. 14A).

The subject motion measuring apparatus 1100 according to the present embodiment includes four cameras 1105, near-infrared illuminators 1106, near-infrared spot array illuminators 1107, and a control unit 1108. The cameras 1105, the near-infrared illuminators 1106, and the near-infrared spot array illuminators 1107 are connected to the control unit 1108 via cables 1109.

<Configuration of the Cameras and the Illuminators>

Referring to FIGS. 17A to 17D, the configuration of the cameras and the illuminators in the subject motion measuring apparatus 1100 will be described below. The four cameras 1105 are disposed like cameras 1120, 1121, 1122, and 1123 in FIG. 17A. The cameras 1120 and 1122 capture moving images around a left eye 1125 while the cameras 1121 and 1123 capture moving images around a right eye 1126.

Figure 17A:
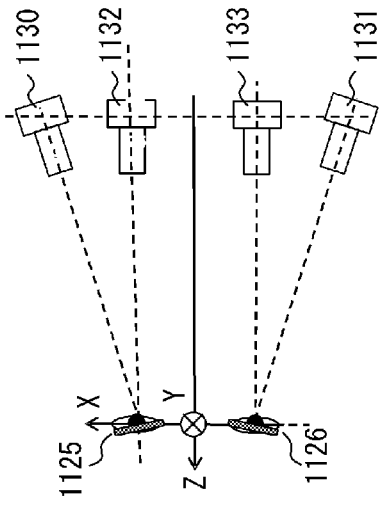
FIGS. 17A to 17D are explanatory drawings illustrating the configuration of the cameras and illuminators.
Figure 17C:
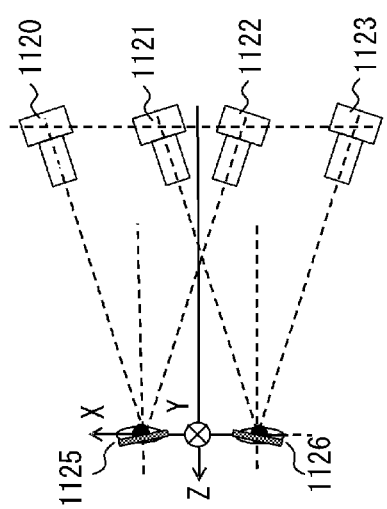
Figure 17B:
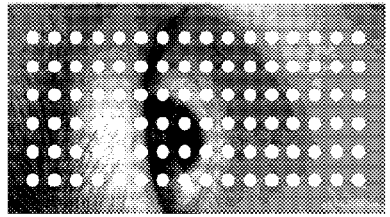

The near-infrared illuminators 1106 are disposed like near-infrared illuminators 1130 and 1131 in FIG. 17B. The near-infrared spot array illuminators 1107 are disposed like near-infrared spot array illuminators 1132 and 1133. The near-infrared illuminator 1130 and the near-infrared spot array illuminator 1132 illuminate a part around the left eye 1125 while the near-infrared illuminator 1131 and the near-infrared spot array illuminator 1133 illuminate a part around the right eye 1126.

Figure 17D:
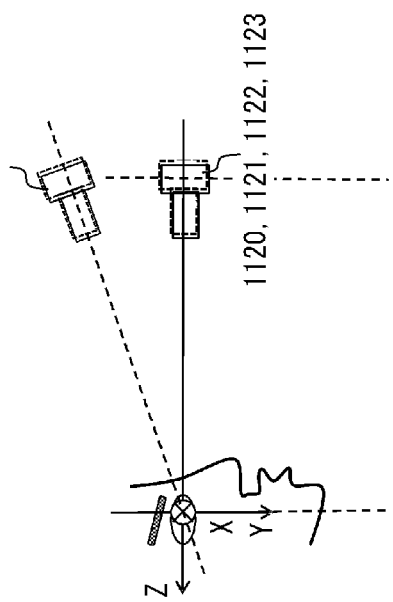

As illustrated in FIG. 17C, an angular difference is made between optical axes such that the shooting range of the camera and the illumination range of near-infrared illumination and near-infrared spot array illumination overlap each other. The near-infrared illumination evenly illuminates the parts around the eyes, whereas the near-infrared spot array illumination generates spots placed at two-dimensional lattice points as illustrated in FIG. 17D.

An illumination light wavelength in the near-infrared illuminator 1106 can be optionally selected from a near-infrared wavelength range. However, if the absorption wavelength of a pigment (e.g., melanin) included in the subject is selected, the contrast of a texture in a patch increases, thereby improving tracking accuracy in the patch tracking steps S512, S900, and S910.

The illumination light wavelength of the near-infrared spot array illuminator 1107 can be also optionally selected from a near-infrared wavelength range. A wavelength with lower absorptivity is suitable for spots of uniform brightness.

As will be described later, the near-infrared spot array illuminators 1107 are used in combination with the near-infrared illuminators 1106 when the patch selecting step S511 is performed. In other steps, only the near-infrared illuminators 1106 are used.

<Configuration of the Control Unit>

Figure 18:
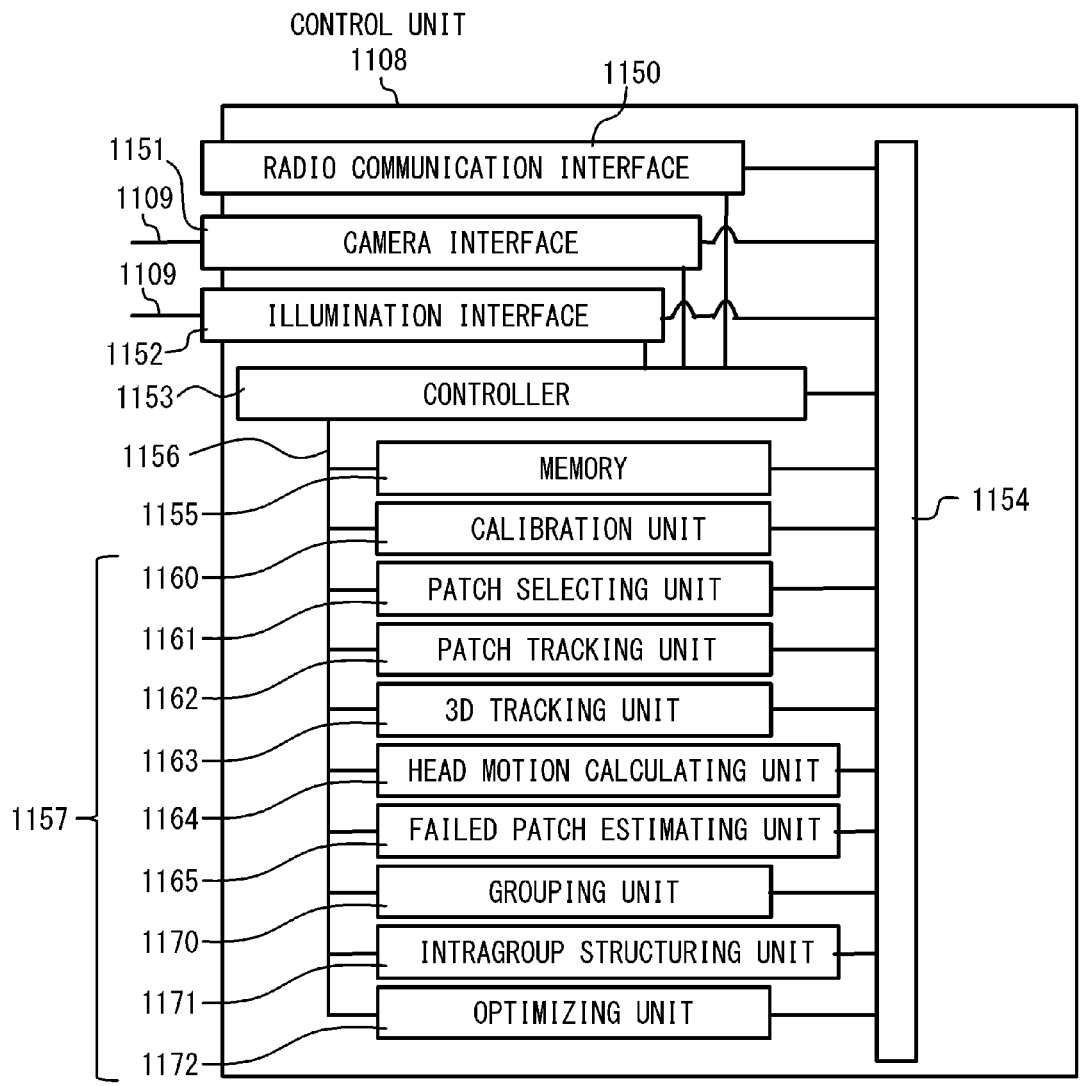
FIG. 18 illustrates a configuration example of the control unit of the subject motion measuring apparatus.

Referring to FIG. 18, the configuration of the control unit 1108 in the subject motion measuring apparatus 1100 will be described below. The control unit 1108 includes a radio communication interface 1150, a camera interface 1151, an illumination interface 1152, a controller (processing unit) 1153, a data bus 1154, a memory 1155, and a plurality of processing elements 1157.

The processing elements 1157 are circuits for performing part of processing of a subject motion measuring method 500. The processing elements 1157 include a calibration unit 1160, a patch selecting unit 1161, a patch tracking unit 1162, a 3D tracking unit 1163, a head motion calculating unit 1164, and a failed patch estimating unit 1165. Furthermore, the processing elements 1157 include a grouping unit 1170, an intragroup structuring unit 1171, and an optimizing unit 1172. Processing performed by the processing elements 1157 corresponds to the steps identified by the same names. For example, the optimizing unit 1172 performs the optimizing step S812. The example of the subject motion measuring method 500 primarily includes common processing such as the subject motion calculating steps S516 and S902. In some cases, slightly different processes are included. The processing elements 1157 can perform such slightly different processes.

The controller (processing unit) 1153 is connected to the radio communication interface 1150, the camera interface 1151, the illumination interface 1152, the data bus 1154, the memory 1155, and the processing elements 1157 via a signal line 1156. Moreover, the radio communication interface 1150, the camera interface 1151, the illumination interface 1152, the memory 1155, and the processing elements 1157 are connected to one another via the data bus 1154. Communications with the controller (processing unit) 1153 are performed by using the signal line 1156, whereas mass data is exchanged by using the data bus 1154.

The controller (processing unit) 1153 can perform the process of the subject motion measuring method 500 by repeating a calculation command to the processing elements 1157 and a connection destination command to the data bus 1154. In other words, the subject motion measuring apparatus 1100 includes the controller (processing unit) 1153 that obtains three-dimensional coordinate data on patches set in first image data and second image data, which are captured by the cameras, based on a parallax between the first image data and the second image data. The controller (processing unit) 1153 can generate motion data on the subject from the three-dimensional coordinate data on the patches and reference coordinate data serving as a criterion for the subject. The controller (processing unit) 1153 generates a translation and a rotation of the subject from the three-dimensional coordinate data on the patches and the reference coordinate data serving as a criterion for the subject.

<Flow of Processing in the Subject Motion Measuring Apparatus 1100>

The processing of the subject motion measuring apparatus 1100 is mostly identical to that of the subject motion measuring apparatus 1000 according to the first embodiment, whereas processing by the patch selecting unit 1161 is different from the patch selecting step S511 of FIG. 4A.

Figure 19:
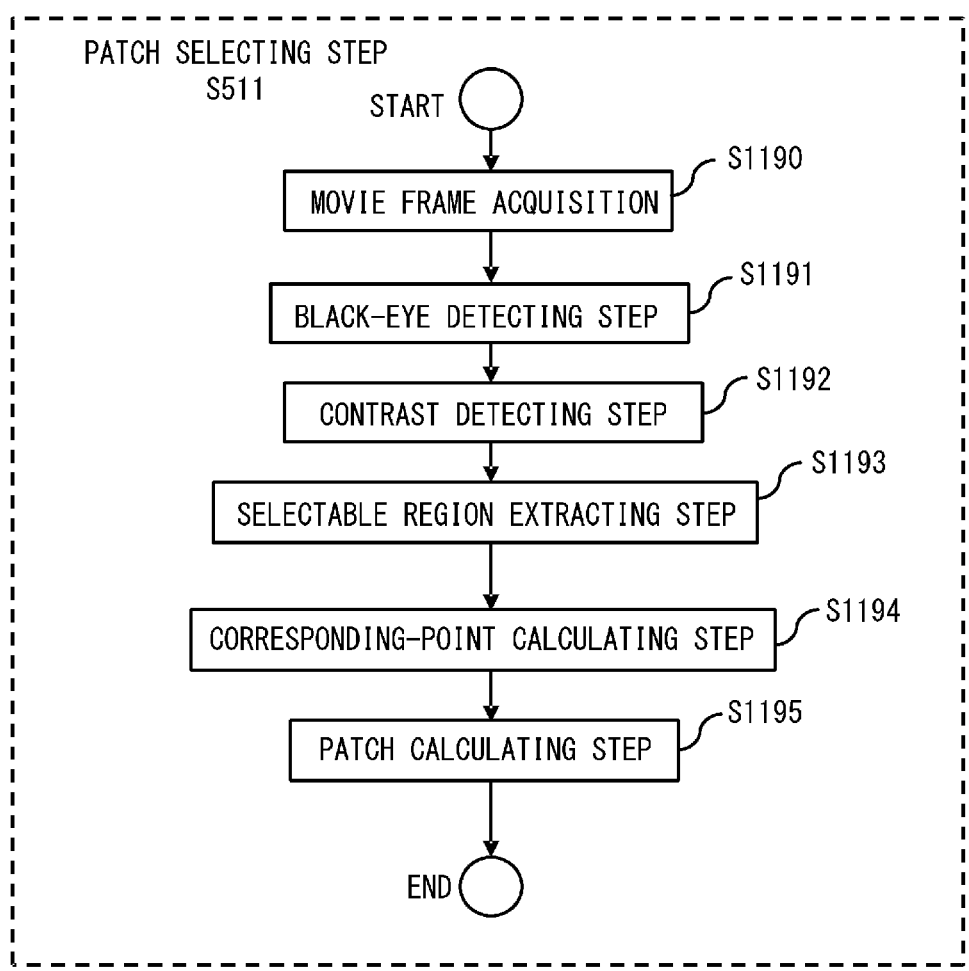
FIG. 19 is a flowchart indicating an example of the process of the patch selecting step.

The patch selecting unit 1161 performs a method using the near-infrared spot array illuminators 1107 instead of the patch selecting step S511 of FIG. 4A. Referring to FIG. 19, an example of processing performed by the patch selecting unit 1161 will be described below.

In movie frame acquisition S1190, a plurality of movie frames are obtained for each of the cameras while switching the illumination of the near-infrared spot array illuminators 1107 with the illuminated near-infrared illuminators 1106.

A black-eye detecting step S1191, a contrast detecting step S1192, and a selectable region extracting step S1193 are identical to the black-eye detecting step S531, the contrast detecting step S532, and the selectable region extracting step S533 of FIG. 4A. However, it is necessary to use only movie frames with the unilluminated near-infrared spot array illuminators 1107. As a result of the selectable region extracting step S1193, reference-plane image data is obtained.

In a corresponding-point calculating step S1194, a movie frame including the pattern of the near-infrared spot array illuminators 1107 is first selected. The shooting time of the movie frame is close to that of the reference-plane image data. Subsequently, the number of spots is counted from one end of the selected movie frame, enabling numbering of the spots.

In a patch calculating step S1195, patch candidates near the spot of the same number are extracted in pieces of reference-plane image data obtained from different cameras. From among the obtained patch candidates, the candidates with high contrasts are used as patches.

If the near-infrared spot array illuminators 1107 are used, deformations on the patches due to the influence of a surface normal may vary among the cameras (FIG. 7B), and such deformations are negligible. Since the range of choices in patch candidates is extended, high-contrast patches can be used with higher tracking accuracy.

A three-dimensional shape measuring method using cameras with spot array illumination is known as an active stereo method. For example, a three-dimensional shape (depth map) near the left eye 1125 can be obtained using the cameras 1120 and 1122 and the near-infrared spot array illuminator 1132. The surface normal of a patch candidate may be calculated from the depth map, and a patch with a surface normal close to the normal of a reference plane (a small change of a patch shape when the subject moves) may be used. In the present embodiment, a spot array pattern is used for illumination. Any pattern is usable when position information in the pattern can be acquired by different cameras.

As described above, according to the second embodiment of the present invention, the wavelength and pattern of illumination light are used, and a calculation is performed with a heavy load by a calculation function serving as a dedicated circuit. This can provide the subject motion measuring apparatus with higher accuracy, a higher frame rate, and a smaller size at the same time.

Third Embodiment

Figure 20:
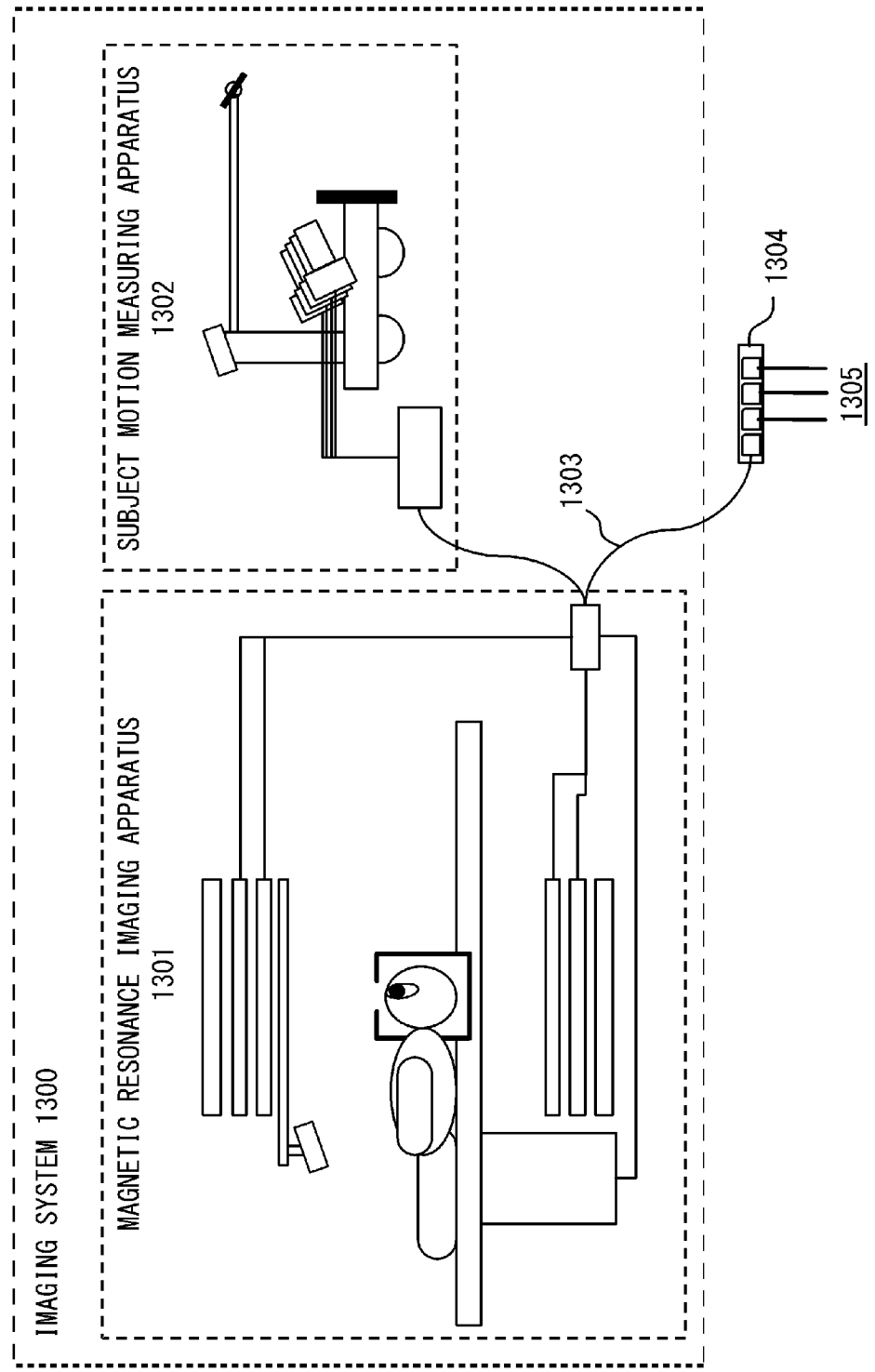
FIG. 20 illustrates a configuration example of a subject motion measuring apparatus according to a third embodiment.

Referring to FIG. 20, an imaging system 1300 according to a third embodiment of the present invention will be described below. FIG. 20 illustrates an example of the configuration of the imaging system 1300 according to the third embodiment. The imaging system 1300 according to the present embodiment includes a magnetic resonance imaging apparatus 1301 and a subject motion measuring apparatus 1302. The magnetic resonance imaging apparatus 1301 and the subject motion measuring apparatus 1302 are connected to each other via a network cable 1303 and can communicate with each other. Moreover, the magnetic resonance imaging apparatus 1301 and the subject motion measuring apparatus 1302 are connected to a LAN 1305 via the network cable 1303 and a switching hub 1304.

The imaging system 1300 according to the present embodiment is applicable to any modality capable of imaging the subject. The imaging system 1300 is applicable to a single modality, for example, a magnetic resonance imaging (MM) apparatus or an X-ray computed tomography (CT) apparatus. The imaging system 1300 is also applicable to a single modality, for example, a positron emission tomography (PET) apparatus. Furthermore, the imaging system 1300 is also applicable to a single modality, for example, a single photon emission computed tomography (SPECT) apparatus. Alternatively, the imaging system according to the present embodiment may be applied to a composite modality, for example, an MR/PET apparatus, a CT/PET apparatus, an MR/SPECT apparatus, or a CT/SPECT apparatus. However, for a specific description, the imaging system according to the present embodiment is assumed to be a magnetic resonance imaging apparatus (MRI apparatus).

<Configuration of the Magnetic Resonance Imaging Apparatus 1301>

Figure 21:
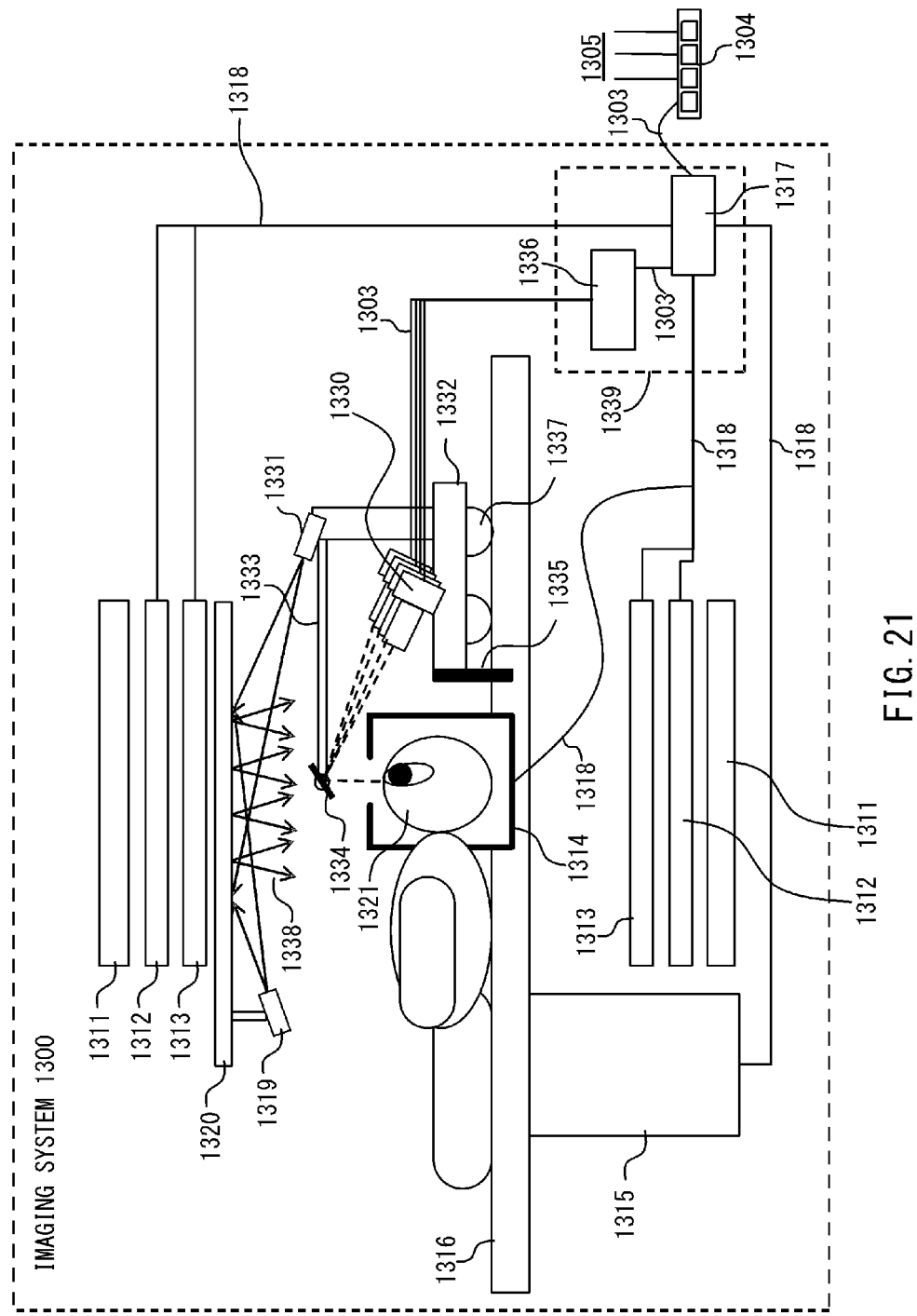
FIG. 21 illustrates a configuration example of a magnetic resonance imaging apparatus.

Referring to FIG. 21, the magnetic resonance imaging apparatus 1301 will be described below. The magnetic resonance imaging apparatus 1301 includes a static magnetic field magnet 1311, a gradient coil 1312, an RF coil 1313, a head coil 1314, a bed 1315, a top 1316, an MRI controller 1317, cables 1318, and a white light illuminator 1319. The MRI controller 1317 is connected to the gradient coil 1312, the RF coil 1313, the head coil 1314, and the bed 1315 via the cable 1318.

The bed 1315 can vertically and longitudinally move the top 1316 placed on the bed. The MRI controller 1317 controls the bed 1315 and delivers a subject 1321 into and out of the system.

Furthermore, the MRI controller 1317 controls a gradient magnetic field via the gradient coil 1312, controls the generation of an RF pulse via the RF coil 1313, and receives a magnetic resonance signal via the head coil 1314. The MRI controller 1317 includes a board computer and generates magnetic resonance data and magnetic-resonance image data based on the magnetic resonance signal. The MRI controller 1317 is connected to an LAN 1305 via the network interface of the board computer. The MRI controller 1317 can receive an imaging command from software on a PC connected to the LAN and transmit the magnetic resonance data and the magnetic-resonance image data to the PC.

The subject motion measuring apparatus 1302 includes an illuminator 1319 for illuminating the subject 1321. The illuminator (white light illuminator) 1319 illuminates a bore inner wall 1320 of a gantry for imaging the subject 1321 and illuminates the subject 1321 with reflected light 1338 from the bore inner wall 1320. The illuminator 1319 is mounted on the bore inner wall 1320. The illuminator 1319 may be mounted on, for example, the top 1316 or a frame (support) 1332, which will be described later. The illuminator 1319 is mounted so as to diagonally illuminate the ceiling (the upper side in FIG. 21) of the bore inner wall 1320. The illuminator 1319 is mounted so as to illuminate a region of the bore inner wall 1320 in front of the head of the subject 1321. The illuminator 1319 is mounted so as to illuminate the subject 1321 with indirect illumination on the bore inner wall 1320 from an opening of the head coil 1314. The reflected light 1338 has the same brightness as indoor light. The illuminator 1319 provides indirect illumination via the bore inner wall 1320, thereby evenly illuminating the subject 1321.

By adjusting the illumination light of the illuminator 1319, first image data and second image data that are captured by a plurality of cameras can be imaged as images of constant brightness. In other words, the first image data and the second image data that are captured by the cameras are imaged as images of constant lightness. The subject 1321 has unevenness on the surface of the skin. Direct illumination on the subject 1321 causes uneven brightness that is likely to generate a shaded region. To reduce a shaded region, the illuminator 1319 is disposed to provide indirect illumination in this configuration.

If the subject 1321 is directly illuminated, direct illumination to the eyes of the subject 1321 may dazzle the subject 1321. However, the illuminator 1319 provides indirect illumination via the bore inner wall 1320, thereby imaging the subject 1321 without dazzling the subject 1321.

The controller (processing unit) 1153 can also perform image processing on the first image data and the second image data with constant lightness. Specifically, the controller (processing unit) 1153 performs histogram analysis on the first image data and the second image data according to the lightness. The controller (processing unit) 1153 acquires a maximum value of lightness in each of the histogram of the first image data and the histogram of the second image data. The controller (processing unit) 1153 adjusts the lightness of the first image data or the second image data with reference to the maximum values of the lightness such that the maximum values of lightness agree with each other. In this way, the first image data and the second image data have the same lightness, achieving uniform image recognition and proper tracking.

<Configuration of the Subject Motion Measuring Apparatus 1302>

Referring to FIG. 21, the subject motion measuring apparatus 1302 will be described below. The subject motion measuring apparatus 1302 includes four cameras 1330, a near-infrared illuminator 1331, the frame (support) 1332, a pole 1333, a mirror 1334, a fastener 1335, and a subject-measuring-apparatus controller 1336. The subject-measuring-apparatus controller 1336 is connected to the cameras 1330 via the network cables 1303. The subject-measuring-apparatus controller 1336 and the cameras 1330 can communicate with each other.

The subject-measuring-apparatus controller 1336 includes a board computer and can execute the software of a subject motion measuring method 500. The board computer of the subject-measuring-apparatus controller 1336 is connected to the MRI controller 1317 and can transmit various kinds of measurement data at a specified time. The board computer can also receive a command from the MRI controller 1317. The subject-measuring-apparatus controller 1336 may be configured without a board computer. The subject-measuring-apparatus controller 1336 may have any configuration that can execute the software of the subject motion measuring method 500. For example, the subject-measuring-apparatus controller 1336 includes processors such as a CPU, a GPU, and an MPU and memory, e.g., ROM or RAM as hardware resources. The subject-measuring-apparatus controller 1336 may be implemented by an application specific integrated circuit (ASIC). The subject-measuring-apparatus controller 1336 may be implemented by a field programmable logic device (FPGA). Alternatively, the subject-measuring-apparatus controller 1336 may be implemented by a complex programmable logic device (CPLD). Alternatively, the subject-measuring-apparatus controller 1336 may be implemented by a simple programmable logic device (SPLD).

The frame 1332 has tires 1337 that are movable on the top 1316 of the bed 1315. The frame 1332 can be fixed at a predetermined position on the top 1316 by the fastener 1335.

The near-infrared illuminator 1331 compensates for the brightness of the white light illuminator 1319 and increases the contrast of textures included in patches.

Referring to FIGS. 22A and 22B, the relationship between the layout of the four cameras 1330 and the openings of the head coil 1314 to be imaged will be described below. The head coil 1314 having a high resolution includes a large number of coils, and the coil near the head has the property of increasing an SN ratio. Since the coils need to be placed over a limited region near the head, the head coil 1314 needs to cover the head of the subject. Moreover, the external wall of the head coil 1314 is lightproof, leading to difficulty in imaging from a part other than the openings. However, the subject suffers from a strong feeling of pressure when the eyes and mouth are covered. Thus, a right-eye opening 1350, a left-eye opening 1351, and a mouth opening 1352 are typically provided (FIG. 22A).

Since the chin and mouth independently move, the imaging result of the mouth opening 1352 is not suitable for measuring a subject motion (skull motion). For this reason, a region around the eyes of the subject is imaged by the four cameras 1330 through the right-eye opening 1350 and the left-eye opening 1351 (FIG. 22B).

When a subject motion is measured from a narrow range, the accuracy of measuring the rotation angle of head shaking tends to decrease. In order to improve the accuracy of measurement, it is necessary to increase a distance between patches in a movie frame. The higher the magnification of photography, the larger the distance between the patches. However, the patches move faster in the movie frame and the motions cause blurs. In order to secure a distance between the patches while avoiding motion blurs, the magnification of photography by the cameras 1330 is set such that a movie frame includes the overall views of the right-eye opening 1350 and the left-eye opening 1351. Moreover, a distance between the patches in the lateral direction can be extended according to a distance between the right eye and the left eye. In order to increase a distance between the patches in the longitudinal direction, the movie frame needs to be placed in portrait orientation. Thus, the cameras 1330 are rotated 90° around the optical axis and are fixed to the frame 1332.

<Flow of Processing in the Imaging System 1300>

During an operation of the imaging system 1300, the magnetic resonance imaging apparatus 1301 can acquire various kinds of measurement data from the subject motion measuring apparatus 1302 at any time. For example, after subject motion data is acquired from the subject motion measuring apparatus 1302, a subject motion is corrected under the control of the gradient coil 1312, thereby generating magnetic-resonance image data with high accuracy.

In the imaging system 1300, the magnetic resonance imaging apparatus 1301 and the subject motion measuring apparatus 1302 are connected to each other via the network cable 1303. Another pattern of connection may be used instead. For example, in the board computer of the MRI controller 1317, the software program of the subject motion measuring method 500 may be executed. In this case, it is necessary to connect the board computer of the MRI controller 1317 to the cameras 1330. Furthermore, if the MRI controller 1317 includes an FPGA board instead of a board computer, an image processing circuit like the control unit 1108 may be packaged on the FPGA board.

As described above, the third embodiment of the present invention provides subject motion information and related information with high accuracy for the magnetic resonance imaging apparatus, thereby providing the imaging system with magnetic-resonance image data of higher image quality and higher added value.

Other Embodiments

Embodiment (s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The technique of the present disclosure can measure a motion of the subject with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-207809, filed on Dec. 15, 2020, which is hereby incorporated by reference herein in its entirety.

What is claimed is:

1. A subject motion measuring apparatus comprising:
at least one memory storing a program; and
at least one processor which, by executing the program, causes the subject motion measuring apparatus to:
acquire three-dimensional coordinate data on a patch set for image data including a predetermined part and a part around the predetermined part of a subject, the image data being acquired from an opening of a head coil in frame data included in moving image data imaged by a camera while the subject is wearing the head coil,
wherein the processor tracks the patch in the moving image data imaged by the camera and generates motion data on a head of the subject on the basis of the three-dimensional coordinate data on the tracked patch.

2. The subject motion measuring apparatus according to claim 1, wherein
the moving image data is imaged by using a plurality of cameras, and
the processor acquires the three-dimensional coordinate data on the patch on the basis of a parallax between first image data and second image data that are captured by the plurality of cameras.

3. The subject motion measuring apparatus according to claim 2, wherein the patch included in the first image data and the patch included in the second image data are identical in size and shape.

4. The subject motion measuring apparatus according to claim 2, wherein the first image data and the second image data are image data obtained by imaging a part around a predetermined part of the subject in different directions.

5. The subject motion measuring apparatus according to claim 4, wherein the predetermined part is a part allowed to be imaged by the plurality of cameras from an opening of a receiving coil that is attached to the subject and receives a magnetic resonance signal.

6. The subject motion measuring apparatus according to claim 4, wherein the predetermined part is an eye or nose of the subject.

7. The subject motion measuring apparatus according to claim 1, wherein the processor generates a translation and a rotation of the subject from the three-dimensional coordinate data on the patch and reference coordinate data serving as a criterion for the subject.

8. The subject motion measuring apparatus according to claim 1, wherein
the moving image data is imaged by using a plurality of cameras, and
first image data and second image data that are captured by the plurality of cameras are image data imaged from different positions.

9. The subject motion measuring apparatus according to claim 8, wherein the patch included in the first image data and the patch included in the second image data are identical in size and shape.

10. The subject motion measuring apparatus according to claim 8, wherein the first image data and the second image data are image data obtained by imaging a part around a predetermined part of the subject in different directions.

11. The subject motion measuring apparatus according to claim 10, wherein the predetermined part is a part allowed to be imaged by the plurality of cameras from an opening of a receiving coil that is attached to the subject and receives a magnetic resonance signal.

12. The subject motion measuring apparatus according to claim 10, wherein the predetermined part is an eye or nose of the subject.

13. The subject motion measuring apparatus according to claim 1, wherein a plurality of the patches are disposed in the frame data, and the plurality of the patches are spaced at least a predetermined distance apart.

14. The subject motion measuring apparatus according to claim 13, further comprising an estimating unit for estimating a position of the patch having moved out of a frame of the frame data on the basis of the patch in the frame from among the patches, when the patch moves out of the frame.

15. The subject motion measuring apparatus according to claim 1, wherein the patch is set in a band region in the frame data.

16. The subject motion measuring apparatus according to claim 15, wherein the processor normalizes a pixel value in the band region.

17. The subject motion measuring apparatus according to claim 1, further comprising an illuminator for illuminating a bore inner wall of a gantry and illuminating the subject with reflected light from the bore inner wall.

18. The subject motion measuring apparatus according to claim 17,
wherein the moving image data is imaged by using a plurality of cameras, and
first image data and second image data that are imaged by the plurality of cameras are captured as images having same lightness by adjusting illumination light of the illuminator.

19. The subject motion measuring apparatus according to claim 1, further comprising an estimating unit for estimating, when the patch moves out of a frame of the frame data, a position of the patch on the basis of reference coordinate data serving as a criterion for the subject.

20. An imaging system for imaging a subject, the imaging system comprising:
the subject motion measuring apparatus for measuring a motion of the subject according to claim 1; and
an imaging apparatus for imaging the subject by correcting a motion of the subject measured by the subject motion measuring apparatus.

21. The imaging system according to claim 20, wherein the imaging apparatus is a magnetic resonance imaging apparatus.

22. The subject motion measuring apparatus according to claim 1, wherein the patch is set in a region around the predetermined part of the subject.

23. The subject motion measuring apparatus according to claim 1, wherein the predetermined part of the subject is a part which moves with a local motion on a surface of the subject, and the part around the predetermined part of the subject is a part which moves with a motion of the head of the subject.

24. A subject motion measuring method comprising the steps of:
acquiring three-dimensional coordinate data on patches set for first image data and second image data including a predetermined part and a part around the predetermined part of a subject, the image data being acquired from an opening of a head coil in the first image data and the second image data on the basis of a parallax between the first image data and the second image data that are imaged by a plurality of cameras while the subject is wearing the head coil; and
generating motion data on a head of the subject from the three-dimensional coordinate data on the patches and reference coordinate data serving as a criterion for the subject.

25. A non-transitory computer readable medium that stores a program, wherein the program causes a computer to execute:
acquiring three-dimensional coordinate data on a patch set for first image data and second image data including a predetermined part and a part around the predetermined part of a subject, the image data being acquired from an opening of a head coil in the first image data and the second image data on the basis of a parallax between the first image data and the second image data that are imaged by a plurality of cameras while the subject is wearing the head coil; and
generating motion data on a head of the subject from the three-dimensional coordinate data on the patch and reference coordinate data serving as a criterion for the subject.

* * * * *